(12) United States Patent  
Berg et al.

(10) Patent No.: US 12,295,730 B2
(45) Date of Patent: May 13, 2025

(54) METHOD OF DETERMINING A CONCENTRATION OF AN ANALYTE IN A BODILY FLUID AND MOBILE DEVICE CONFIGURED FOR DETERMINING A CONCENTRATION OF AN ANALYTE IN A BODILY FLUID

(71) Applicant: Roche Diabetes Care, Inc., Indianapolis, IN (US)

(72) Inventors: Max Berg, Mannheim (DE); Fredrik Hailer, Limburgerhof (DE); Bernd Limburg, Soergenloch (DE); Daria Skuridina, Berlin (DE); Volker Tuerck, Berlin (DE); Momme Winkelnkemper, Berlin (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 455 days.

(21) Appl. No.: 17/553,382

(22) Filed: Dec. 16, 2021

(65) Prior Publication Data

US 2022/0104736 A1 Apr. 7, 2022

Related U.S. Application Data

(63) Continuation of application No. PCT/EP2020/067444, filed on Jun. 23, 2020.

(30) Foreign Application Priority Data

Jun. 26, 2019 (EP) .................................. 19 182 555

(51) Int. Cl.
*A61B 5/145* (2006.01)
*A61B 5/15* (2006.01)
(Continued)

(52) U.S. Cl.
CPC .... *A61B 5/14546* (2013.01); *A61B 5/150358* (2013.01); *G01N 21/78* (2013.01);
(Continued)

(58) Field of Classification Search
CPC ... G06T 7/0012; G06T 7/0014; G06T 7/0016; G06T 7/80
See application file for complete search history.

(56) References Cited

U.S. PATENT DOCUMENTS 9,230,509 B2 1/2016 Van Der Vleuten
9,842,381 B2 12/2017 Douady-Pleven et al.
(Continued)

FOREIGN PATENT DOCUMENTS

JP 2005-202749 A 7/2005
JP 2007-188465 A 7/2007
(Continued)

OTHER PUBLICATIONS

International Search Report and Written Opinion of the International Searching Authority, PCT/EP2020/067444, Sep. 18, 2020, 10 pages.
(Continued)

*Primary Examiner* — Wen W Huang
(74) *Attorney, Agent, or Firm* — Bose McKinney & Evans LLP

(57) ABSTRACT

A method of determining concentration of an analyte in a body fluid using a mobile device having a camera is disclosed. In the inventive method, the camera is used to take a series of calibration images of a region of interest of an object. The calibration images differ in their brightness. A key calibration figure is derived from each calibration image, the key calibration images being characteristic for a tone mapping function of the mobile device. A probable tone mapping function of the mobile device is determined by (Continued)

taking into account the key calibration figures. An analysis image is taken of at least part of a test field of an optical test strip, the test field having a body fluid applied thereto. Analyte concentration is determined from the analysis image of the test field by taking into account the probable tone mapping function of the mobile device.

18 Claims, 7 Drawing Sheets

(51) Int. Cl.
  *G01N 21/78* (2006.01)
  *G01N 21/84* (2006.01)
  *G06T 5/92* (2024.01)
  *G06T 7/00* (2017.01)
  *G06T 7/80* (2017.01)

(52) U.S. Cl.
  CPC .......... *G01N 21/8483* (2013.01); *G06T 5/92* (2024.01); *G06T 7/0012* (2013.01); *G06T 7/80* (2017.01); *G01N 2021/8488* (2013.01); *G01N 2201/0221* (2013.01)

(56) References Cited

U.S. PATENT DOCUMENTS

| | | |
|---|---|---|
| 2009/0231469 A1 | 9/2009 | Kato |
| 2011/0298819 A1 | 12/2011 | Evans et al. |
| 2013/0126712 A1 | 5/2013 | Petrich et al. |
| 2014/0072189 A1 | 3/2014 | Jena et al. |
| 2014/0078193 A1* | 3/2014 | Barnhoefer .......... G09G 3/3607 345/87 |
| 2015/0233898 A1* | 8/2015 | Chen .................. G01N 21/8483 422/404 |
| 2015/0359458 A1* | 12/2015 | Erickson ................... G06T 7/90 382/133 |
| 2017/0139572 A1* | 5/2017 | Sunkavalli .......... G06F 3/04845 |
| 2017/0161881 A1* | 6/2017 | Najaf-Zadeh ........... G06F 3/147 |
| 2017/0330529 A1 | 11/2017 | Van Mourik et al. |
| 2018/0024049 A1 | 1/2018 | Shyam et al. |
| 2019/0226985 A1* | 7/2019 | Roberts ................ G01N 21/274 |
| 2019/0279549 A1* | 9/2019 | Shin ...................... G09G 3/2007 |
| 2020/0078781 A1* | 3/2020 | Beckley .................... B01L 3/50 |
| 2020/0316720 A1* | 10/2020 | Liu ....................... G01B 11/303 |

FOREIGN PATENT DOCUMENTS

| | | |
|---|---|---|
| JP | 2009-245429 A | 10/2009 |
| JP | 2015-533211 A | 11/2015 |
| JP | 2016-163722 A | 9/2016 |
| WO | WO 2007/079843 A2 | 7/2007 |
| WO | WO 2016/132243 A1 | 8/2016 |
| WO | WO 2019/023376 A1 | 1/2019 |
| WO | WO 2019/081460 A1 | 5/2019 |
| WO | WO 2019/081541 A1 | 5/2019 |

OTHER PUBLICATIONS

Hönes et al., Diabetes Technology and Therapeutics, vol. 10, Supplement 1, 2008, pp. 10-26.

Burggraaff et al., Standardized Spectral and Radiometric Calibration of Consumer Cameras, arxiv.org, Cornell University Library, 201, Olin Library Cornell University, Ithaca, NY 14853, Jun. 7, 2019, 27 pages.

Budianto et al., Strip Test Analysis Using Image Processing for Diagnosing Diabetes and Kidney Stone Based on Smartphone, 2018 International Electronics Symposium on Knowledge Creation and Intelligent Computing (IES-KCIC), IEEE, Oct. 29, 2018, pp. 235-241.

* cited by examiner

METHOD OF DETERMINING A CONCENTRATION OF AN ANALYTE IN A BODILY FLUID AND MOBILE DEVICE CONFIGURED FOR DETERMINING A CONCENTRATION OF AN ANALYTE IN A BODILY FLUID

RELATED APPLICATIONS

This application is a continuation of PCT/EP2020/067444, filed Jun. 23, 2020, which claims priority to EP 19 182 555.3, filed Jun. 26, 2019, the entire disclosures of both of which are hereby incorporated herein by reference.

BACKGROUND

This disclosure teaches a method of determining a concentration of an analyte in a bodily fluid by using a mobile device having a camera. This disclosure further relates to a computer program. This disclosure further relates to a mobile device having a camera and a processor, the processor being configured to perform for determining a concentration of an analyte in a bodily fluid. This disclosure further relates to a kit for determining a concentration of an analyte in a bodily fluid, the kit comprising at least one mobile device having a camera and a processor and at least one optical test strip having at least one test field.

In the field of medical diagnostics, in many cases, one or more analytes have to be detected in samples of a body fluid, such as blood, interstitial fluid, urine, saliva or other types of body fluids. Examples of analytes to be detected are glucose, triglycerides, lactate, cholesterol or other types of analytes typically present in these body fluids. According to the concentration and/or the presence of the analyte, an appropriate treatment may be chosen, if necessary. Without narrowing the scope, this disclosure specifically will be described with respect to blood glucose measurements. It shall be noted, however, that this disclosure may also be used for other types of analytical measurements using test strips.

Generally, devices and methods known to the skilled person make use of test strips comprising one or more test chemistries, which, in the presence of the analyte to be detected, are capable of performing one or more detectable detection reactions, such as optically detectable detection reactions. With regard to these test chemistries, reference may be made, e.g., to J. Hoenes et al.: The Technology Behind Glucose Meters: Test Strips, Diabetes Technology & Therapeutics, Volume 10, Supplement 1, 2008, S-10 to S-26. Other types of test chemistries are possible and may be used for performing this disclosure.

Typically, one or more optically detectable changes in the test chemistry are monitored, in order to derive the concentration of the at least one analyte to be detected from these changes. For detecting the at least one change of optical properties of the test field, various types of detectors, specifically customized detectors, are known in the art. Thus, various types of light sources for illuminating the test fields as well as various types of detectors are known.

Further, besides using customized detectors which are specifically developed for the purpose of optically detecting changes in the test chemistry comprised by corresponding test elements, recent developments aim at using widely available devices such as smartphones. However, when consumer-electronics devices having a camera, such as smartphones, are employed in order to determine analyte concentrations, new challenges, in particular concerning the accuracy, arise. This may specifically be due to the processing of image data, e.g., by correction functions, that is generally used by smartphones to obtain a more pleasing image. Said image data processing steps usually concern a variety of aspects of the image data. In particular, they can affect the accuracy of the determination of the analyte concentration that is based on the image data. Examples for the processing of image data can be found, e.g., in U.S. Publication No. 2011/0298819 A1, U.S. Pat. No. 9,230,509 B2, U.S. Publication No. 2017/0330529 A1 and U.S. Pat. No. 9,842,381 B2.

U.S. Publication No. 2014/072189 A1 discloses a system and a method for analysis of colorimetric test strip strips and disease management. The system can include an accessory that is operably coupled to a mobile device, the mobile device acquiring and/or analyzing images of the colorimetric test strips. The light box accessory can be detachably attached to the mobile device, or made to remain attached to the mobile device, but with the capability of having the light box accessory removed from the field of view of the camera for general photography purposes. In other embodiments, an image containing known calibration color(s) and reagent area(s) is obtained sans the light box for comparison with a previous calibration image to model changes in ambient lighting conditions and determine a color correction function. The correction can be applied to the detected reagent area color(s) for matching between the detected reagent area color(s) and reference color(s) on the reference chart. Optionally, the information can be processed and displayed to provide feedback, as well as transmitted to a health provider for analysis.

Oliver Burggraaff et al.: "Standardized spectral and radiometric calibration of consumer cameras", ARXIV.ORG, CORNELL UNIVERSITY LIBRARY, 201, OLIN LIBRARY CORNELL UNIVERSITY, ITHACA, NY 14853, 7 Jun. 2019, discloses that consumer cameras, particularly onboard smartphones and UAVs, are now commonly used as scientific instruments. However, their data processing pipelines are not optimized for quantitative radiometry and their calibration is more complex than that of scientific cameras. The lack of a standardized calibration methodology limits the interoperability between devices and, in the ever-changing market, ultimately the lifespan of projects using them. The publication presents a standardized methodology and database (SPECTACLE) for spectral and radiometric calibrations of consumer cameras, including linearity, bias variations, read-out noise, dark current, ISO speed and gain, flat-field, and RGB spectral response. This includes golden standard ground-truth methods and do-it-yourself methods suitable for non-experts. Applying this methodology to seven popular cameras, the authors found high linearity in RAW but not JPEG data, inter-pixel gain variations>400% correlated with large-scale bias and read-out noise patterns, non-trivial ISO speed normalization functions, flat-field correction factors varying by up to 2.79 over the field of view, and both similarities and differences in spectral response. Moreover, these results differed wildly between camera models, highlighting the importance of standardization and a centralized database.

The use of customer-electronics devices having a camera, such as smartphones, in the field of determining analyte concentrations using optical test strips is a rather recent development and still faces many challenges. Thus, with customized detectors, the image data is usually available in an unprocessed form. Alternatively, process steps applied to the data are generally known and may be chosen to facilitate the determination of the analyte concentration. However, methods of determining a concentration of an analyte in a bodily fluid based on using consumer-electronics devices having a camera, such as smartphones, usually have to cope without knowledge on if and/or how the available image data has been processed.

SUMMARY

This disclosure teaches methods and devices for determining a concentration of an analyte in a bodily fluid, which address the above-mentioned technical challenges of methods and devices using mobile devices such as consumer-electronics mobile devices, specifically multipurpose mobile devices, which are not dedicated to analytical measurements, such as smartphones or tablet computers.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "calibration figure," "region of interest," and "camera," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure a method of determining a concentration of an analyte in a bodily fluid by using a mobile device having a camera is disclosed. The method comprises the following steps, which may specifically be performed in the given order. Still, a different order may also be possible. It may further be possible to perform two or more of the method steps fully or partially simultaneously. It may further be possible to perform one or more method steps or even all of the method steps once or repeatedly. The method may comprise additional method steps which are not listed herein. Generally, the method of determining a concentration of an analyte in a bodily fluid by using a mobile device having a camera comprises the following steps:

a) taking a series of calibration images of at least one region of interest of an object by using the camera, wherein the calibration images differ in their brightness;

b) deriving from each calibration image of the series taken in step a) at least one key calibration figure characteristic for a tone mapping function of the mobile device;

c) determining at least one probable tone mapping function of the mobile device by taking into account the key calibration figures from the calibration images of the series taken in step a);

d) taking at least one analysis image of at least part of a test field of an optical test strip, the test field having the bodily fluid applied thereto; and e) determining the concentration of the analyte in the bodily fluid from the analysis image of the test field by taking into account the probable tone mapping function of the mobile device.

The disclosed method of determining a concentration of an analyte in a bodily fluid by using a mobile device having a camera comprising the steps just described may also be referred to as the method of determining a concentration of an analyte in a bodily fluid.

The term "analyte" as used herein is a broad term and is to be given its ordinary and customary meaning to a person of ordinary skill in the art and is not to be limited to a special or customized meaning. The term specifically may refer, without limitation, to arbitrary chemical, biochemical or biological substance, component or compound, such as a molecule, e.g., glucose, triglycerides, lactate or cholesterol.

The term "determining a concentration of an analyte," which may also be referred to as an analytical measurement or determination of an analyte concentration, as used herein is a broad term and is to be given its ordinary and customary meaning to a person of ordinary skill in the art and is not to be limited to a special or customized meaning. The term may specifically refer, without limitation, to a qualitative and/or quantitative determination of at least one analyte in a sample. The result of the analytical measurement, as an example, may be the concentration of the analyte and/or the presence or absence of the analyte to be determined.

The term "bodily fluid" (also referred to herein as "body fluid") as used herein is a broad term and is to be given its ordinary and customary meaning to a person of ordinary skill in the art and is not to be limited to a special or customized meaning. The term may specifically refer, without limitation, to a liquid sample comprising at least one bodily fluid, such as blood, interstitial fluid, urine, saliva or the like.

The term "mobile device" as used herein is a broad term and is to be given its ordinary and customary meaning to a person of ordinary skill in the art and is not to be limited to a special or customized meaning. The term may specifically refer, without limitation, to a mobile electronics device, more specifically to a mobile communication device comprising at least one processor. The mobile device may specifically be a cell phone or smartphone. Additionally or alternatively, as will be outlined in further detail below, the mobile device may also refer to a tablet computer or any other type of portable computer having at least one camera.

The term "camera" as used herein is a broad term and is to be given its ordinary and customary meaning to a person of ordinary skill in the art and is not to be limited to a special or customized meaning. The term may specifically refer, without limitation, to a device configured for recording spatially resolved optical data, such as one or more images. The camera may specifically comprise one or more imaging devices, such as camera chips or imaging chips, e.g., CCD and/or CMOS chips. The camera, in particular the imaging device, may comprise a one-dimensional or two-dimensional array of image sensors, such as pixels. As an example, the camera may comprise at least 10 pixels in at least one dimension, such as at least 10 pixels in each dimension. It shall be noted, however, that other cameras are also feasible. This disclosure shall specifically be applicable to cameras as usually used in mobile applications such as notebook computers, tablets or, specifically, cell phones such as smart phones. Thus, specifically, the camera may be part of a mobile device which, besides the at least one camera, comprises one or more data processing devices such as one or more data processors. Other cameras, however, are feasible. The camera, besides at least one camera chip or imaging chip, may comprise further elements, such as one or more optical elements, e.g., one or more lenses. As an example, the camera may be a fix-focus camera, having at least one lens, which is fixedly adjusted with respect to the camera. Alternatively, however, the camera may also comprise one or more variable lenses which may be adjusted, automatically or manually.

The term "image" as used herein is a broad term and is to be given its ordinary and customary meaning to a person of ordinary skill in the art and is not to be limited to a special or customized meaning. The term may specifically refer, without limitation, to a set of spatially resolved optical data. The set of spatially resolved optical data may specifically comprise optical information on a region of an object. The image may also be a partial image of a larger image, e.g., a subset of spatially resolved optical data of a larger set of spatially resolved optical data. Thus, the image of an object may be subdivided into a plurality of two or more partial images which, each by itself, may be considered as an image.

The set of spatially resolved optical data may in particular be generated, acquired or recorded simultaneously, e.g., by taking an image of a certain exposure time with the mobile device. The set of spatially resolved optical data, herein also referred to as the data set, may be generated in a two-step process. In a first step, spatially resolved optical data may be generated, acquired or recorded by the imaging device, such as the CCD or CMOS chip, when taking the image. This data set may also be referred to as the first data set, raw data or unprocessed data. The first data set may not be available or accessible to a user of the mobile device. In a second step the first data set may be subjected to one or several processing steps, e.g., by the at least one processor of the mobile device, to create a second data set that is based on or derived from the first data set. In particular, the tone mapping function of the mobile device may be applied to the first data set to create the second data set. The second data set may also be referred to as processed data. The second data set may in particular be used by the mobile device for a graphical representation of the image, e.g., on a screen. The second data set may further be available and/or accessible on the mobile device, e.g., to a user of the mobile device. The image may in particular comprise the second data set. The imaging device used to create the first data set may be the imaging device of the camera of the mobile device, e.g., the CCD and/or CMOS chip. The set of spatially resolved optical data may specifically be a digital data set. In particular, the first data set and the second data set may each be a digital data set. The spatially resolved optical data set comprised by the image may be received as an output data set from the mobile device, specifically from the camera of the mobile device, the processor of the camera or another processor of the mobile device, e.g., in form of an image file. In the context of this disclosure, images may particularly be taken in the form of the calibration images and the analysis image.

In particular, the first data set may comprise a plurality of electronic readings, also referred to as counts, originating from the imaging device, specifically from the image sensors, e.g., the pixels of the camera chip. Thus, the first data set may comprise a plurality of numerical values, wherein each numerical value may represent a number of counts detected by a pixel of the camera chip. In particular, each pixel may be represented by more than one numerical value, e.g., by three numerical values, wherein the three numerical values may represent the number of counts in the red, green and blue channel, respectively. A representation of the counts in a color space other than the RGB color space is also possible, wherein "RGB" stands for "Red Green Blue." The second data may comprise a plurality of numerical values that may be received or deduced from the plurality of numerical values originating from the first set by applying the processing step, in particular the tone mapping function. Thus, as an example, the image may comprise a one-dimensional or two-dimensional array of data. The spatially resolved optical data may comprise information, e.g., on the colors and/or brightness of an object that is imaged.

The term "series of image," such as used in the context of "series of calibration image," as used herein is a broad term and is to be given its ordinary and customary meaning to a person of ordinary skill in the art and is not to be limited to a special or customized meaning. The term may specifically refer, without limitation, to a plurality of images. The images of the plurality of images may be acquired simultaneously or at different times, such as in a predetermined time sequence. The images of the series of images may be images of one and the same object, taken at the same time or taken at different times, or may be images of different parts of the object. Thus, as an example, the series of calibration images may be a series of different fields or regions of a grey scale step wedge or may even be partial images of a larger image of the grey scale step wedge. Other possibilities exist.

As described above and as further described below, the term pixel may refer to the image sensors of the camera, specifically of the imaging device of the camera. Each pixel may generate optical information, e.g., in the form of counts. This optical information may be part of the first set of data and, specifically in a processed form, of the second set of data. Consequently, when referring to "pixels," reference is either made to the units of image information generated by or derived from the single pixels of the camera chip, or to the single pixels of the camera chip directly.

The term "calibration image" as used herein is a broad term and is to be given its ordinary and customary meaning to a person of ordinary skill in the art and is not to be limited to a special or customized meaning. The term may specifically refer, without limitation, to an image that may be taken and/or used in the process of checking, assessing, evaluating or gathering information about the settings of a device or a method and/or in the process of adjusting, modifying or correcting the settings of a device or a method. In particular, as a result of the calibration, the settings of the device or the method may be brought in line with target settings. Thus, the calibration image and in particular the series of calibration images may specifically be used to gain information on the settings of the mobile device, specifically on the tone mapping function, more specifically to determine a probable tone mapping function as will be described in further detail below.

The term "series of calibration images" as used herein is a broad term and is to be given its ordinary and customary meaning to a person of ordinary skill in the art and is not to be limited to a special or customized meaning. The term may specifically refer, without limitation, to plurality of at least two calibration images, wherein the calibration images are taken by one and the same imaging device, such as one and the same camera, in a timely sequential manner. Thus, as an example, the series of calibration images may comprise 2 images, 3 images, 5 images or more images, such as 10 images or more. Specifically, the images of the series may be taken at short intervals, wherein the intervals may differ or may have a constant value. The intervals may specifically have a value of 100 ms to 1 s, more specifically 200 ms to 800 ms, most specifically 250 ms to 500 ms. Thus, as an example, the series of calibration images may comprise 5 images which may be taken within a timespan of 1 s. The series of calibration images may be taken without the user taking notice. The settings of the camera may be varied from image to image in a controlled manner, such as by varying a parameter value as described in further detail below. The images of the series of calibration images differ in their brightness.

The term "brightness" as used herein is a broad term and is to be given its ordinary and customary meaning to a person of ordinary skill in the art and is not to be limited to a special or customized meaning. The term may specifically refer, without limitation, to a property characterizing an image or a subsection thereof, e.g., one or several pixels, wherein the property quantifies, represents or relates to a light intensity that is impinged upon the imaging device when generating the image, specifically when generating the first set of spatially resolved optical data. Specifically, the brightness of an image may be quantified as an arithmetic mean of the red, green, and blue color coordinates when the RGB color space is used. Alternatively, each color channel may deliver a brightness value. In particular, the brightness of an image or a subsection thereof may be represented by a numerical value referred to as a brightness value. The brightness value may be part of the spatially resolved optical data set comprised by the image. Alternatively, the brightness value may be derivable from the spatially resolved optical data set comprised by the image. The brightness value as generated by the imaging device may be subjected to processing steps, which yield a processed brightness value. Specifically, the numerical value of the processed brightness value may differ from the numerical value of the brightness value, e.g., of the original brightness value, generated by the imaging device. For distinguishing purposes, the original brightness value may specifically be referred to as brightness value generated by the imaging device. The processed brightness value, for example the brightness value of an image after applying a processing function, such as for example a tone mapping function, to the original brightness value, may particularly be referred to as brightness value of an image taken by the camera. In particular, the processed brightness value may be part of or may be derivable from the spatially resolved optical data set of the image.

The term "region of interest" as used herein is a broad term and is to be given its ordinary and customary meaning to a person of ordinary skill in the art and is not to be limited to a special or customized meaning. The term may specifically refer, without limitation, to a section or a segment or a partition of an object, wherein the section, segment or partition is identified for a particular purpose. Thus, the region of interest may, e.g., be a delimited surface area of the object. Alternatively, the region of interest may refer to a subset of data of an image, wherein the subset represents the section, segment or partition of the object. As an example, the region of interest may comprise certain information or information may be deducible from it.

The term "key calibration figure" as used herein is a broad term and is to be given its ordinary and customary meaning to a person of ordinary skill in the art and is not to be limited to a special or customized meaning. The term may specifically refer, without limitation, to at least one numerical value, which may be used in the process of checking, assessing, evaluating or gathering information about the settings of a device or a method and/or in the process of adjusting, modifying or correcting the settings of a device or a method. In particular, the key calibration figure may be or may comprise the numerical brightness value of the region of interest of the calibration image.

The term "tone mapping function" as used herein is a broad term and is to be given its ordinary and customary meaning to a person of ordinary skill in the art and is not to be limited to a special or customized meaning. The term may specifically refer, without limitation, to an arbitrary correlation, which allows assigning to a first brightness value, which may be generated, detected or recorded by the imaging device, a second brightness value. The assignment may comprise at least one mathematical operation, e.g., a multiplication with at least one factor or another type of mathematical operation. The first brightness value may be part of the first data set or raw data. The second brightness value may be part of the second data set or processed data. In particular, the second brightness value may be part of the spatially resolved optical set of data comprised by the image, in particular the image file. The second brightness value determined by the tone mapping function may in particular be used for a graphical representation of the image. The correlation may in particular be a function, specifically a continuous or discontinuous function, a curve, a look-up table, an operator or any other means describing the correlation between the first brightness value and the second brightness value. The tone mapping function may in particular be a so-called gamma correction, in particular the sRGB gamma correction of the sRGB color space, wherein "sRGB" stands for "standard Red Green Blue." The gamma correction may also be referred to as gamma correction function. The tone mapping function may be invertible. The tone mapping function may be a monotonously increasing function, in particular a strictly monotonously increasing function. Alternatively, the tone mapping function may be a monotonously decreasing function, in particular a strictly monotonously decreasing function. The tone mapping function may be non-linear. The tone mapping function used by the mobile device may not be known and/or may not be accessible to a user of the mobile device.

The term "probable tone mapping function" as used herein is a broad term and is to be given its ordinary and customary meaning to a person of ordinary skill in the art and is not to be limited to a special or customized meaning. The term specifically may refer, without limitation, to a tone mapping function that is likely used in a certain process or by a certain device, e.g., the mobile device. Alternatively, the probable tone mapping function may refer to a tone mapping function that approximates the tone mapping function that is actually used in a certain process or by a certain device, e.g., the mobile device. In particular, the probable tone mapping function may be the tone mapping function that is likely used by the mobile device to assign to the first brightness value as generated by the imaging device a second brightness value, which may be part of the spatially resolved optical data set of the image. Alternatively, the probable tone mapping function may approximate the tone mapping function that is actually used by the mobile device to assign to the first brightness value the second brightness value. The probable tone mapping function may be invertible. The inverted probable tone mapping function may be applied to the image, in particular the calibration image and/or the analysis image. In particular, the inverted probable tone mapping function may be applied to the data of the spatially resolved optical data set of the calibration image and the analysis image, to determine probable raw or unprocessed data as generated by the imaging device of the camera. Specifically, the inverted probable tone mapping function may be applied to the key calibration figure to determine at least one probable calibration measurement figure. Further, the inverted probable tone mapping function may be applied to a key analysis figure further described below to determine at least one probable analysis measurement figure.

The term "determining a function," is a broad term and is to be given its ordinary and customary meaning to a person of ordinary skill in the art, and is not to be limited to a special or customized meaning. The term specifically may refer, without limitation, to appointing or specifying the function according to or based on a preceding process or predetermined criteria. Thus, determining the probable tone mapping function may comprise calculating the function, approximating the function, fitting the function, extrapolating the function and/or choosing the function, e.g., from a predetermined set of functions, particularly after checking the suitability of the function. Other processes for determining the probable tone mapping functions may also be feasible. Specifically other analytical, non-analytical and iterative processes may be used for determining the probable tone mapping function.

The term "analysis image" as used herein is a broad term and is to be given its ordinary and customary meaning to a person of ordinary skill in the art and is not to be limited to a special or customized meaning. The term may specifically refer, without limitation, to an image that may be used in the process of determining an analyte concentration. Step d) comprises taking at least one analysis image of at least part of the test field of the optical test strip, the test field having the bodily fluid applied thereto. Specifically, a plurality of analysis images may be taken, such as 2, 3, 5 or even more analysis images.

The term "test field" as used herein is a broad term and is to be given its ordinary and customary meaning to a person of ordinary skill in the art and is not to be limited to a special or customized meaning. The term may specifically refer, without limitation, to a coherent amount of at least one test chemical, such as to an area, e.g., an area of round, polygonal or rectangular shape, having one or more layers of material, with at least one layer of the test field having the test chemical comprised therein. Other layers may be present in the test field, providing specific optical properties such as reflective properties, providing spreading properties for spreading the sample or providing separation properties such as for separating off particulate components of the sample, such as cellular components.

The term "optical test strip" as used herein is a broad term and is to be given its ordinary and customary meaning to a person of ordinary skill in the art and is not to be limited to a special or customized meaning. The term may specifically refer, without limitation, to an arbitrary element or device comprising at least one strip-shaped carrier, with the at least one test field applied thereto or integrated therein, the element being configured for detecting the analyte or determining the concentration of the analyte in a liquid sample, such as in the bodily fluid, specifically in a sample of the bodily fluid. The optical test strip may also be referred to as a test strip or a test element. These test strips are generally widely in use and available. One test strip may carry a single test field or a plurality of test fields having identical or different test chemicals comprised therein. The optical test strip, in particular the test field comprising the test chemical, may specifically undergo a detection reaction, particularly a coloration reaction, in the presence of the at least one analyte, specifically a coloration reaction, wherein the color formation may be related, e.g., proportional to, the concentration of the analyte. Since the presence, the absence and/or the concentration of the analyte may be detectable by the detection reaction, the detection reaction may also be referred to as analyte detection reaction. Some basic principles on test elements and reagents that may also be used within the scope of this disclosure are described, e.g., in J. Hones et al.: Diabetes Technology and Therapeutics, Vol. 10, Supplement 1, 2008, pp.10-26.

Steps d)-e) may be performed repeatedly. In particular, steps a)-c) may be performed only once initially for a plurality of repetitions of steps d)-e) or each time before performing steps d)-e) or at a predetermined frequency. The frequency may be at least one of: a temporal frequency; a frequency defined by a predetermined number of repetitions of steps d-e).

Step a) comprises taking the series of calibration images of the at least one region of interest of the object. The series may comprise at least two calibration images, specifically at least three calibration images, more specifically at least five calibration images. The object may comprise at least one element of the group consisting of: the optical test strip; a sheet of paper, specifically a sheet of white paper. Specifically, the object may comprise the optical test strip and the analysis image may coincide with at least one of the calibration images, such that the analysis image may be taken as part of the series of calibration images. Further, the series of calibration images may be taken with the bodily fluid applied to the test field, wherein at least one of the calibration images may comprise the part of the test field. The region of interest of the object may comprise at least one element of the group consisting of: a white field; a black field; a grey field; a grey scale step wedge. In particular, the object may comprise at least two regions of interest, specifically one black field or one first grey field and one white field or one second grey field. The first grey field and the second grey field may differ from each other in grey shade. Further each calibration image may comprise the at least two regions of interest, specifically one black field or one first grey field and one white field or one second grey field. Further, a physical brightness ratio between the two regions of interest may be known.

Step b) comprises deriving from each calibration image of the series taken in step a) at least one key calibration figure characteristic for a tone mapping function of the mobile device. In particular, for each calibration image the key calibration figure may be derived from at least one brightness value of the region of interest of the calibration image. In particular, the key calibration figure may comprise or may be the at least one brightness value of the region of interest of the calibration image. The brightness value may in particular be the second brightness value as described above. The key calibration figure may specifically comprise at least one of the following: at least one of the brightness values of the region of interest of the calibration image; at least one average brightness value derived from a plurality of the brightness values of the region of interest of the calibration image. The calibration images of the series of calibration images differ in their brightness. In step a), the brightness of the calibration images may be actively varied, specifically in a stepwise fashion. The brightness of the calibration images may be varied in step a) by varying a parameter value of at least one of the following parameters: an exposure time; a light sensitivity of the image sensor of the camera, specifically an ISO sensitivity of the image sensor; a light intensity of an illuminant, specifically an LED of the mobile device, particularly of the camera. It was found that varying the exposure time yielded more stable and reliable results, specifically a better defined stepwise variation of the brightness values of the data set of the image, than varying the light sensitivity of the image sensor of the camera. The exposure time may in particular be from 0.1 ms to 100 ms, specifically from 0.2 ms to 25 ms, more specifically from 0.5 ms to 15 ms.

The term "parameter value" as used herein is a broad term and is to be given its ordinary and customary meaning to a person of ordinary skill in the art and is not to be limited to a special or customized meaning. The term may specifically refer, without limitation, to a value of a variable or a quantity that affects a process or a device. The parameter value may be characteristic for a setting of the process or the device and may affect its outcome or product.

The parameter values may be selected in such a way that the brightness value of the region of interest of the calibration image taken with the parameter values may be part of a predetermined brightness value range. The brightness value range may in particular be determined by at least one structural features of the camera of the mobile device, such as, e.g., the analog-to-digital converter, also referred to as ADC, and/or the resolution of the image. The parameter values may be selected such that the brightness value may be from 10% to 100%, specifically 10% to 90%, more specifically 20% to 90%, of the maximum value of counts convertible by the ADC. In the case of an image with a resolution of 8 bit, the brightness parameter values may be selected such that the brightness value may be from 25 counts to 255 counts, specifically from 25 counts to 230 counts, more specifically from 50 counts to 230 counts. In particular, the parameter values may be essentially proportional to the brightness values detected by the image sensor of the camera.

Step c) comprises determining the at least one probable tone mapping function of the mobile device by taking into account the key calibration figures from the calibration images of the series taken in step a). Step c) may further comprise determining at least one sampling point, specifically at least one pair of values, for each calibration image, wherein the sampling point may comprise the key calibration figure derived from one of the calibration images and the parameter value used for taking said calibration image.

The term "sampling point" as used herein is a broad term and is to be given its ordinary and customary meaning to a person of ordinary skill in the art and is not to be limited to a special or customized meaning. The term may specifically refer, without limitation, to a point as definable by a pair of values, wherein the point may contribute in determining, e.g., by computing, checking or approximating, a function, a curve or another type of correlation. In particular, the sampling point may be used to determine the probable tone mapping function. The sampling point associated with the calibration image may specifically comprise the brightness value of the calibration image, specifically the processed brightness value that may be part of or derivable from the set of spatially resolved optical data of the calibration image, and the parameter value used for the generation of the calibration image, specifically the exposure time.

Step c) may further comprise determining the probable tone mapping function by at least one of the following: determining a correlation, particularly a fit curve, for the sampling points of the series of calibration images; choosing a correlation, in particular a function, from a predetermined set of correlations, wherein the chosen correlation fits the sampling points of the series of calibration images. In particular, the set of predetermined functions may comprise the sRGB gamma correction, wherein "sRGB" stands for "standard Red Green Blue."

Step e) comprises determining the concentration of the analyte in the bodily fluid from the analysis image of the test field by taking into account the probable tone mapping function of the mobile device. Step e) may in particular comprise deriving at least one key analysis figure from at least one brightness value of at least one part of the analysis image showing the at least one part of the test field.

The term "key analysis figure" as used herein is a broad term and is to be given its ordinary and customary meaning to a person of ordinary skill in the art and is not to be limited to a special or customized meaning. The term may specifically refer, without limitation, to at least one numerical value, which may be used in an analytical process, specifically in the determining of the concentration of the analyte in the bodily fluid. In particular, the key analysis figure may comprise at least one of the following: the at least one of the brightness value of the part of the analysis image showing the test field; at least one average brightness value derived from a plurality of the brightness values of the part of the analysis image showing the test field.

Further, from each key analysis figure the probable analyte measurement figure may be derived by applying the inverted probable tone mapping function to the key analysis figure. The probable analyte measurement figure may comprise at least one probable brightness value, wherein the probable brightness value may approximate the brightness value detected by the imaging device, e.g., the image sensor, of the camera, when imaging the part of the test field having the bodily fluid applied thereto. Further, in step e) the analyte concentration may be determined from the probable analyte measurement figure by using a predetermined correlation between the probable analyte measurement figure and the analyte concentration.

Step c) comprises determining at least one probable tone mapping function of the mobile device by taking into account the key calibration figures from the calibration images of the series taken in step a). Step c) may further comprise applying the inverted probable tone mapping function to the key calibration figures to determine for each key calibration figure at least one probable calibration measurement figure, wherein determining the probable tone mapping function comprises choosing a predetermined tone mapping function from a group of predetermined tone mapping functions.

The probable calibration measurement figure may comprise at least one probable brightness value, wherein the probable brightness value may approximate the brightness value detected by the imaging device, e.g., the image sensor, of the camera, when imaging the region of interest of the object, specifically the optical test strip. The chosen predetermined tone mapping function may in particular be the sRGB gamma correction. Further, a linearity of a relationship between test points, particularly pairs of test values, may be checked, wherein each test point may comprise the probable calibration measurement figure and the parameter value. The chosen predetermined tone mapping function may be confirmed as the probable tone mapping function if the relationship between the test points is classified as linear. If the relationship between the test points is classified as non-linear, a residual correlation between the test points, in particular a fit curve, may be determined, wherein the chosen predetermined tone mapping function and the residual correlation may together fit the test points. The residual correlation between the test points may in particular be approximated by a parabola, a parabolic function or a parabolic fit. Specifically, in step c) the probable tone mapping function may be determined by taking into account both the chosen predetermined tone mapping function and the residual correlation. In particular, the probable tone mapping function may comprise two steps, which may be carried out or applied sequentially. In particular, the probable tone mapping function may comprise the sRGB gamma correction, which may be applied to data of the data set of the image in a first step, and a residual correlation, e.g., a parabolic correlation, which may be applied in a second step.

Additionally or alternatively, the chosen predetermined tone mapping function may be selected from a set of predetermined tone mapping functions, such as a plurality of predetermined tone mapping functions. In particular, from the plurality of predetermined tone mapping functions, a tone mapping function which leads to a relationship between the test points closest to a linear relationship, may be selected.

Additionally or alternatively, the probable tone mapping function may be derived by determining a residual correlation between the test points, specifically by a fit curve. For example, the residual correlation, e.g., the fit curve, may specifically be approximated by an arbitrary function, e.g., by a polynomial function, such as by a polynomial fit.

Summarizing, the following three methods may specifically be used for determining the probable tone mapping function in step c):

(A) choosing at least one predetermined tone mapping function, such as the sRGB tone mapping function, and applying the inverted predetermined tone mapping function to the key calibration figures, thereby generating a set of probable calibration measurement figures and, subsequently, applying a residual correlation function, such as a parabolic function, in order to correct for residual non-linearities between the probable calibration measurement figures and the parameter values, wherein the probable tone mapping function is the combination of the predetermined tone mapping function and the inverted residual correlation function;

(B) selecting the probable tone mapping function from a set of tone mapping functions by using at least one selection criterion, such as selecting from the set of tone mapping functions the tone mapping function which, when the inverted tone mapping function is applied to the key calibration figures, thereby generating probable calibration measurement figures, leads to the best linear relationship between the probable calibration measurement figures and the parameter values;

(C) determining the probable tone mapping function by generating a fit function and/or fit curve which correlates the parameter values and the key calibration figures. Specifically, the fit function may be generated such that it may link the parameter values and the key calibration figures.

These methods may also be combined, such as by, firstly, applying method (B) and subsequently correcting for residual errors by applying the residual correction step of method (A). Further, other methods of determining the probable tone mapping function may be possible.

The method of determining a concentration of an analyte in a bodily fluid may further comprise step f):

f) setting the tone mapping function of the mobile device to a linear tone mapping function, specifically a tone mapping function characterized by a proportionality between a brightness value detected by an image sensor, e.g., an original brightness value, and a brightness value of an image taken by the camera, e.g., a processed brightness value.

Step f) specifically may precede step a). In particular, the tone mapping function, to which the tone mapping function is set, may be such that the brightness value of an image taken by the camera, e.g., the processed brightness value, is equal to the brightness value detected by the image sensor, e.g., the original brightness value. In particular, the tone mapping function, to which the tone mapping function is set, may be such that the processed brightness value equals the original brightness value. Thus, the tone mapping function may be selected such that, by applying the tone mapping function to the brightness value, the brightness value, for example, remains unchanged, thereby generating a processed brightness value equal to the original brightness value. Further, a linearity of a relationship between sampling points may be checked, wherein each sampling point may comprise the key calibration figure derived from one of the calibration images and the parameter value used for taking said calibration image. The linear tone mapping function, to which the tone mapping function was set, may further be determined as the probable tone mapping function, if the relationship between the sampling points is classified as linear.

In this case, the key analysis figure derivable from the analysis image may be proportional to, specifically equal to, the brightness value as detected by the imaging device of the camera. Thus, the concentration of the analyte in the bodily fluid may be determined from the key analysis figure.

Step e) comprises determining the concentration of the analyte in the bodily fluid from the analysis image of the test field by taking into account the probable tone mapping function of the mobile device. In step e) the analyte concentration may specifically be determined by taking into account a brightness ratio between the test field having the bodily fluid applied and the region of interest of the object. The brightness ratio between the test field having the bodily fluid applied and the region of interest of the object may in particular be or may equal at least one deviation factor for the at least one analysis image. The analysis image may for example be characterized by the parameter value used for taking the analysis image and the key analysis figure comprising at least one brightness value. The deviation factor may specifically describe the ratio between the parameter value of the analysis image and the parameter value of a point on a curve representing the probable tone mapping function. The point on the curve may for example be characterized by the parameter value and the key calibration figure comprising the same value as the key analysis figure, specifically the brightness value. The probable tone mapping function may specifically be represented in a half-logarithmic fashion, wherein the parameter value may be represented in a logarithmic fashion, while the brightness value may be represented in a linear, specifically non-logarithmic, fashion.

Further, a plurality of at least two, specifically three, more specifically five, analysis images may be used, wherein the at least one deviation factor may be determined for each analysis image, wherein at least one averaged deviation factor may be determined from the plurality of deviation factors.

Furthermore, the object may comprise the optical test strip and each analysis image may coincide with one of the calibration images such that the analysis images are taken as part of the series of calibration images.

The brightness ratio of the test field with the bodily fluid applied and the region of interest, e.g., the white field, may be set in relation to a reference brightness ratio. The reference brightness ratio may for example be the brightness ratio between the test field without the bodily fluid applied and the region of interest. Specifically, the reference brightness ratio may be or may comprise the brightness ratio between the dry test field, prior to application of the bodily fluid and the region of interest, for example the white field. In this case, an image of the test field without the bodily fluid applied may be taken as part of the series of calibration images or as a separate image. Alternatively, the reference brightness ratio may be the brightness ratio between a reference field on the optical test strip and the region of interest. In particular, the reference brightness ratio may be or may comprise the brightness ratio between the reference field, such as a field representing the color of the test field prior to application of the bodily fluid, and the region of interest, e.g., the white field. In this case, the reference brightness ratio may be deduced from the analysis image. From the ratio between the two brightness ratios, e.g., the brightness ratio between the test field having the bodily fluid applied and the region of interest of the object and the reference brightness ratio, the analyte concentration may be determined such as by using at least one of: a code curve; a look-up table; a neuronal network.

The mobile device used in the method may comprise at least one storing device, also referred to as a storage device. The probable tone mapping function determined in step c) may be stored in the at least one storing device of the mobile device. In particular, after a repeated performance of steps a)-c) a plurality of determined probable tone mapping functions may be stored in the storing device. The probable tone mapping function determined in step c) may be compared to at least one of the probable tone mapping functions stored in the storing device. Further, the probable tone mapping function determined in step c) may be discarded, if a deviation of the probable tone mapping function determined in step c) from at least one of the stored probable tone mapping functions exceeds a predetermined threshold value.

Further, statistical data, e.g., an average value and/or a standard deviation, of at least one fit parameter, which may be used to determine the probable tone mapping function in step c), may be deduced from the plurality of probable tone mapping functions stored. The statistical data may specifically be used to evaluate, specifically to accept or reject a most recently determined probable tone mapping function. The most recent tone mapping function may be rejected if the at least one fit parameter of the most recent tone mapping curve deviates from the average of the fit parameter by a predetermined threshold value or more. The most recent tone mapping function may be accepted if the at least one fit parameter of the most recent tone mapping curve deviates from the average of the fit parameter by less than a predetermined threshold value. The use of statistical data in the determination of the probable tone mapping function may be particularly advantageous. Light reflections may lead to unusable calibration images and/or unusable or erroneous probable tone mapping functions, which may be identified as such more easily by using the statistical data.

Method steps b), c) and e) of the method of determining a concentration of an analyte in a bodily fluid by using a mobile device having a camera, may be computer-implemented. Further, steps a) and d) may be computer-prompted.

In the following different optional embodiments of the method of determining a concentration of an analyte in a bodily fluid are described.

In one embodiment the probable tone mapping function may be determined by determining from each calibration image the at least one sampling point, wherein each sampling point may comprise the key calibration figure derived from the calibration image and the parameter value of the camera used when taking the calibration image. The probable tone mapping function may then be determined in step c) using the sampling points. Specifically, a correlation, particularly a fit curve, in accordance with the sampling points of the series of calibration images may be determined as the probable tone mapping function. Additionally or alternatively, a correlation, in particular a function, may be chosen as the probable tone mapping function from a predetermined set of correlations, wherein the chosen correlation fits the sampling points of the series of calibration images. At least one key analysis figure may then be derived from at least one brightness value of at least one part of the analysis image showing the at least part of the test field as part of step e). The key analysis figure may specifically comprise at least one of the following: the at least one of the brightness values of the part of the analysis image showing the test field; at least one average brightness value derived from a plurality of the brightness values of the part of the analysis image showing the test field. Further, from each key analysis figure at least one probable measurement figure may be derived by applying the inverted probable tone mapping function to the key analysis figure. The probable measurement figure may specifically comprise at least one probable brightness value, wherein the probable brightness value may approximate the brightness value detected by the image sensor of the camera. In step e) the analyte concentration may then be determined from the probable measurement figure by using a predetermined correlation between the probable measurement figure and the analyte concentration.

In a further embodiment, step c) of the method may comprise determining the probable tone mapping function by choosing or assuming a correlation, in particular a function, as the probable tone mapping function from a predetermined set of correlations. The correlation chosen or assumed as the probable tone mapping function may particularly be the sRGB gamma correction. The choice or assumption may then be checked by applying the inverted probable tone mapping function to the key calibration figures to determine for each key calibration figure at least one possible measurement figure. The linearity of the relationship between the test points, particularly test pairs of values, may then be checked as part of step c), wherein each test point may comprise the possible measurement figure and the parameter value. The chosen or assumed predetermined tone mapping function may then be determined or confirmed as the probable tone mapping function as part of step c) if the relationship between the test points is classified as linear. Classification may depend on a threshold value quantifying a deviation from a strictly linear relationship. Further, if the relationship between the test points is classified as non-linear, a residual correlation between the test points, in particular a fit curve, may be determined, wherein the residual correlation may fit the test points. The residual correlation between the test points may particularly be approximated by a at least one of: a parabola; a parabolic function; a parabolic fit. The probable tone mapping function determined in step c) may then comprise two functions that may, e.g., be applied in a two step process. In particular, in step c) the probable tone mapping function may be determined by taking into account both the chosen predetermined tone mapping function and the residual correlation.

In a further embodiment, the method may further comprise step f), as described above. Thus, the tone mapping function of the mobile device may be set to a linear tone mapping function, specifically a tone mapping function characterized by a proportionality between a brightness value detected by an image sensor and a brightness value of an image taken by the camera. Step f) may particularly precede step a) of the method, such that the tone mapping function actually used by the mobile device may be known if the mobile device allows the setting of the tone mapping function as described in step f). As part of step c) sampling points comprising the key calibration figure derived from one of the calibration images and the parameter value used for taking said calibration image may be formed. Further the linearity of the relationship between sampling points may be checked. Thus, it may in particular be checked or tested, whether the tone mapping function of the mobile device may actually be set to the linear tone mapping function in step f). The linear tone mapping function, to which the tone mapping function of the mobile device may be set in step f), may be determined as the probable tone mapping curve in step c) if the relationship between the sampling points is classified as linear. Classification may depend on a threshold value quantifying a deviation from a strictly linear relationship. If the tone mapping function of the mobile device is settable, the probable tone mapping function determined in step c) may particularly be the tone mapping function actually used by the mobile device. Further, if the tone mapping function is set to a linear tone mapping function, specifically to a tone mapping function that outputs the input data, step e) may comprise determining the analyte concentration by either using the key analysis figure derived from the analysis image without the application of the inverted probable tone mapping function or by applying the inverted probable tone mapping function to the key analysis figure.

In a further aspect of this disclosure, a computer program is disclosed, the computer program comprising computer-executable instructions which, when the computer program is executed by a computer, specifically a processor of a mobile device, cause the computer to carry out method steps b), c) and e) and optionally f) of the method of determining a concentration of an analyte in a bodily fluid by using a mobile device having a camera as described above or as further described below. Regarding terms and definitions reference may be made to the terms and definitions as disclosed in the context of the method of determining a concentration of an analyte in a bodily fluid by using a mobile device having a camera. The computer program may further comprise computer-executable instructions which, when the computer program is executed by the computer, cause the computer to prompt the taking of the series of calibration images according to step a) of the method. The computer program may further comprise computer-executable instructions which, when the computer program is executed by the computer, cause the computer to prompt the taking of the at least one analysis image according to step d) of the method.

In a further aspect of this disclosure, a mobile device having a camera and at least one processor, is disclosed the processor being configured to perform the following steps:

i.) prompting a user to take a series of calibration images of at least one region of interest of an object by using the camera, wherein the calibration images differ in their brightness;

ii.) deriving from each calibration image of the series taken in step i.) at least one key calibration figure characteristic for a tone mapping function of the mobile device;

iii.) determining at least one probable tone mapping function of the mobile device by taking into account the key calibration figures from the calibration images of the series taken in step i.);

iv.) prompting the user to take at least one analysis image of at least part of a test field of an optical test strip, the test field having the bodily fluid applied thereto; and v.) determining a concentration of an analyte in a bodily fluid from the analysis image of the test field by taking into account the probable tone mapping function of the mobile device.

Regarding terms and definitions reference may be made to the terms and definitions as disclosed in the context of the method of determining a concentration of an analyte in a bodily fluid by using a mobile device having a camera. The mobile device, specifically the processor, may be configured to perform the steps of the method of determining a concentration of an analyte in a bodily fluid by using a mobile device having a camera as described above or as further described below.

The term "prompting" as used herein is a broad term and is to be given its ordinary and customary meaning to a person of ordinary skill in the art and is not to be limited to a special or customized meaning. The term may specifically refer, without limitation, to summoning, inviting or requesting an action. In particular, a user may be prompted to carry out an action such as taking a picture, e.g., by receiving a message on a screen of the mobile device and/or via an audible signal. Other forms of prompting may be feasible.

In a further aspect of this disclosure, a kit for determining a concentration of an analyte in a bodily fluid is disclosed, the kit comprising:

at least one mobile device having a camera and at least one processor as described above or as further described below; and at least one optical test strip having at least one test field.

The optical test strip may in particular be an optical test strip as described above or as further described below. Specifically, the optical test strip may comprise at least one region of interest.

Regarding terms and definitions reference may be made to the terms and definitions as disclosed in the context of the method of determining a concentration of an analyte in a bodily fluid by using a mobile device having a camera. The optical test strip may in particular comprise at least one region of interest.

The methods and devices disclosed above in the different aspects of this disclosure have numerous advantages over methods and devices described in the art. Mobile devices having a camera usually apply tone mapping functions to the raw data acquired by the imaging device of the camera to generate the processed data set on the basis of the raw data. The processed data is generally used to display a graphical representation of the image taken by the camera. The tone mapping function is generally a non-linear function. In most cases, neither the tone mapping function used nor the raw data are accessible or made available, e.g., to a user or a developer of an application. Instead, the processed data set is generally accessible to the user and/or developer of an application, e.g., in form of an image file. Further, it is often not possible for the user or the application developer to set the tone mapping function of the mobile device to a specific, e.g., known, tone mapping function. If an analysis image of the at least one part of the test field of the optical test strip is used to determine the concentration of the analyte in a bodily fluid applied to the test field, determination of the analyte concentration using the processed data may lead to inaccurate analyte concentrations, specifically due to the non-linearity of the tone mapping function used by the mobile device. Thus, determining a probable tone mapping function, and taking into account the probable tone mapping function when determining the analyte concentration, may increase the accuracy of the determined analyte concentration as compared to methods known in the art.

Further, the methods and devices disclosed above in the different aspects of this disclosure may be particularly advantageous due to its high flexibility, which may allow the use of this method with a high number of mobile devices. Usually, different mobile devices, such as different smart phones, may come with different restrictions which may allow or impede the use of a certain method with a particular mobile device. The method according to this disclosure may be used with a large number of mobile devices due to its flexibility. Specifically, this implies a great user-friendliness since users may change their mobile devices and keep using the same, familiar method, e.g., for determining blood glucose.

Summarizing and without excluding further possible embodiments, the following embodiments may be envisaged:

Embodiment 1: A method of determining a concentration of an analyte in a bodily fluid by using a mobile device having a camera, the method comprising:
- a) taking a series of calibration images of at least one region of interest of an object by using the camera, wherein the calibration images differ in their brightness;
- b) deriving from each calibration image of the series taken in step a) at least one key calibration figure characteristic for a tone mapping function of the mobile device;
- c) determining at least one probable tone mapping function of the mobile device by taking into account the key calibration figures from the calibration images of the series taken in step a);
- d) taking at least one analysis image of at least part of a test field of an optical test strip, the test field having the bodily fluid applied thereto; and
- e) determining the concentration of the analyte in the bodily fluid from the analysis image of the test field by taking into account the probable tone mapping function of the mobile device.

Embodiment 2: The method according to the preceding embodiment, wherein the analyte is glucose.

Embodiment 3: The method according to any one of the preceding embodiments, wherein the bodily fluid is blood.

Embodiment 4: The method according to any one of the preceding embodiments, wherein steps d)-e) are performed repeatedly, wherein steps a)-c) either only once initially for a plurality of repetitions of steps d)-e) or each time before performing steps d)-e) or at a predetermined frequency.

Embodiment 5: The method according to the preceding embodiment, wherein the frequency is at least one of: a temporal frequency; a frequency defined by a predetermined number of repetitions of steps d-e).

Embodiments 6: The method according to any one of the preceding embodiments, wherein the series comprises at least two calibration images, specifically at least three calibration images, more specifically at least five calibration images.

Embodiment 7: The method according to any one of the preceding embodiments, wherein the object comprises at least one element of the group consisting of: the optical test strip; a sheet of paper, specifically a sheet of white paper.

Embodiment 8: The method according to any one of the preceding embodiments, wherein the object comprises the optical test strip, wherein the analysis image coincides with at least one of the calibration images, such that the analysis image is taken as part of the series of calibration images.

Embodiment 9: The method according to the preceding embodiment, wherein the series of calibration images is taken with the bodily fluid applied to the test field, wherein at least one of the calibration images comprises the part of the test field.

Embodiment 10: The method according to any one of the preceding embodiments, wherein the region of interest comprises at least one element of the group consisting of: a white field; a black field; a grey field; a grey scale step wedge.

Embodiment 11: The method according to any one of the preceding embodiments, wherein each calibration image comprises at least two regions of interest, specifically one black field and one white field specifically one black field or one first grey field and one white field or one second grey field.

Embodiment 12: The method according to the preceding embodiment, wherein a physical brightness ratio between the two regions of interest is known.

Embodiment 13: The method according to any one of the preceding embodiments, wherein for each calibration image the key calibration figure is derived from at least one brightness value of the region of interest of the calibration image.

Embodiment 14: The method according to the preceding embodiment, wherein the key calibration figure comprises at least one of the following: at least one of the brightness values of the region of interest of the calibration image; at least one average brightness value derived from a plurality of the brightness values of the region of interest of the calibration image.

Embodiment 15: The method according to any one of the preceding embodiments, wherein, in step a), the brightness of the calibration images is actively varied, specifically in a stepwise fashion.

Embodiment 16: The method according to any one of the preceding embodiments, wherein the brightness of the calibration images is varied in step a) by varying a parameter value of at least one of the following parameters: an exposure time; a light sensitivity of an image sensor of the camera, specifically an ISO sensitivity of the image sensor; a light intensity of an illuminant, specifically an LED of the mobile device, particularly of the camera.

Embodiment 17: The method according to the preceding embodiment, wherein the parameter values are selected in such a way that the brightness value of the region of interest of the calibration image taken with the parameter values is part of a predetermined brightness value range.

Embodiment 18: The method according to any one of the two preceding embodiments, wherein the parameter values are essentially proportional to the brightness values detected by the image sensor of the camera.

Embodiment 19: The method according to any one of the three preceding embodiments, wherein step c) comprises determining at least one sampling point, specifically at least one pair of values, for each calibration image, wherein the sampling point comprises the key calibration figure and the parameter value.

Embodiment 20: The method according to the preceding embodiment, wherein step c) comprises determining the probable tone mapping function by at least one of the following: determining a correlation, particularly a fit curve, for the sampling points of the series of calibration images; choosing a correlation, in particular a function, from a predetermined set of correlations, wherein the chosen correlation fits the sampling points of the series of calibration images.

Embodiment 21: The method according to the preceding embodiment, wherein the set of predetermined functions comprises the sRGB gamma correction.

Embodiment 22: The method according to any one of the preceding embodiments, wherein step e) comprises deriving at least one key analysis figure from at least one brightness value of at least one part of the analysis image showing the at least one part of the test field.

Embodiment 23: The method according to the preceding embodiment, wherein the key analysis figure comprises at least one of the following: the at least one of the brightness values of the part of the analysis image showing the test field; at least one average brightness value derived from a plurality of the brightness values of the part of the analysis image showing the test field.

Embodiment 24: The method according to any one of the two the preceding embodiments, wherein from each key analysis figure at least one probable analyte measurement figure is derived by applying the inverted probable tone mapping function to the key analysis figure.

Embodiment 25: The method according to the preceding embodiment, wherein the probable analyte measurement figure comprises at least one probable brightness value, wherein the probable brightness value approximates the brightness value detected by the image sensor of the camera when imaging the part of the test field having the bodily fluid applied thereto.

Embodiment 26: The method according to any one of the two preceding embodiments, wherein in step e) the analyte concentration is determined from the probable analyte measurement figure by using a predetermined correlation between the probable analyte measurement figure and the analyte concentration.

Embodiment 27: The method according to any one of the preceding embodiments, wherein step c) of the method comprises applying the inverted probable tone mapping function to the key calibration figures to determine for each key calibration figure at least one probable calibration measurement figure, wherein the tone mapping function is chosen from a group of predetermined tone mapping functions.

Embodiment 28: The method according to the preceding embodiment, wherein the chosen predetermined tone mapping function is the sRGB gamma correction.

Embodiment 29: The method according to any one of the two preceding embodiments, wherein a linearity of a relationship between test points, particularly test pairs of values, is checked, wherein each test point comprises the probable calibration measurement figure and the parameter value.

Embodiment 30: The method according to the preceding embodiment, wherein the chosen predetermined tone mapping function is determined as the probable tone mapping function if the relationship between the test points is classified as linear.

Embodiment 31: The method according to any one of the two preceding embodiments, wherein, if the relationship between the test points is classified as non-linear, a residual correlation between the test points, in particular a fit curve, is determined, wherein the residual correlation fits the test points.

Embodiment 32: The method according to the preceding embodiment, wherein the residual correlation between the test points is approximated by at least one of: a parabola; a parabolic function; a parabolic fit.

Embodiment 33: The method according to any one of the two preceding embodiments, wherein in step c) the probable tone mapping function is determined by taking into account both the chosen predetermined tone mapping function and the residual correlation.

Embodiment 34: The method according to any one of the preceding embodiments, wherein the method further comprises:
 f) setting the tone mapping function of the mobile device to a linear tone mapping function, specifically a tone mapping function characterized by a proportionality between a brightness value detected by an image sensor, e.g., an original brightness value, and a brightness value of an image taken by the camera, e.g., a processed brightness value.

Embodiment 35: The method according to the preceding embodiment, wherein step f) precedes step a).

Embodiment 36: The method according to any one of the two preceding embodiments, wherein a linearity of a relationship between sampling points is checked, wherein each sampling point comprises the key calibration figure derived from one of the calibration images and the parameter value used for taking said calibration image.

Embodiment 37: The method according to the preceding embodiment, wherein the linear tone mapping curve is determined as the probable tone mapping curve if the relationship between the sampling points is classified as linear.

Embodiment 38: The method according to any one of the preceding embodiments, wherein in step e) the analyte concentration is determined from a brightness ratio between the test field having the bodily fluid applied and the region of interest of the object.

Embodiment 39: The method according to the preceding embodiment, wherein the brightness ratio between the test field having the bodily fluid applied and the region of interest of the object is or equals at least one deviation factor for the at least one analysis image, wherein the analysis image is characterized by the key analysis figure comprising at least one brightness value and the parameter value used for taking the analysis image, wherein the deviation factor describes the ratio between the parameter value of the analysis image and the parameter value of a point on a curve representing the probable tone mapping function, wherein the point on the curve is characterized by the parameter value and the brightness value, wherein the brightness value of the point on the curve and the key analysis figure are identical.

Embodiment 40: The method according to the preceding embodiment, wherein the probable tone mapping function is represented in a half-logarithmic fashion, wherein the parameter value is represented in a logarithmic fashion, while the brightness value is represented in a linear, specifically non-logarithmic, fashion.

Embodiment 41: The method according to any one of the two preceding embodiments, wherein a plurality of at least two, specifically three, more specifically five, analysis images are used, wherein the at least one deviation factor is determined for each analysis image, wherein at least one averaged deviation factor is determined from the plurality of deviation factors.

Embodiment 42: The method according to the preceding embodiment, wherein the object comprises the optical test strip, wherein each analysis image coincides with at least one calibration image such that the analysis images are taken as part of the series of calibration images.

Embodiment 43: The method according to any one of the preceding embodiments, wherein the probable tone mapping function determined in step c) is stored in at least one storing device of the mobile device.

Embodiment 44: The method according to the preceding embodiment, wherein after a repeated performance of steps a)-c) a plurality of determined tone mapping functions is stored in the storing device.

Embodiment 45: The method according to the preceding embodiment, wherein the tone mapping function determined in step c) is compared to at least one of the tone mapping functions stored in the storing device.

Embodiment 46: The method according to the preceding embodiment, wherein the tone mapping function determined in step c) is discarded, if a deviation of the tone mapping function determined in step c) from at least one of the stored tone mapping functions exceeds a predetermined threshold value.

Embodiment 47: The method according to any one of the preceding embodiments, wherein method steps b), c) and e) are computer-implemented.

Embodiment 48: The method according to any one of the preceding embodiments, wherein, further, steps a) and d) are computer-prompted.

Embodiment 49: A computer program comprising computer-executable instructions which, when the computer program is executed by a computer, specifically a processor of a mobile device, cause the computer to carry out method steps b), c) and e) and optionally f) of any one of the preceding claims.

Embodiment 50: The computer program according to the preceding embodiment, wherein the computer program further comprises computer-executable instructions which, when the computer program is executed by the computer, cause the computer to prompt the taking of the series of calibration images according to step a) of the method.

Embodiment 51: The computer program according to any one of the two preceding embodiments, wherein the computer program further comprises computer-executable instructions which, when the computer program is executed by the computer, cause the computer to prompt the taking of the at least one analysis image according to step d) of the method.

Embodiment 52: A mobile device having a camera and a processor, the processor being configured to perform the following steps:
  i.) prompting a user to take a series of calibration images of at least one region of interest of an object by using the camera, wherein the calibration images differ in their brightness;
  ii.) deriving from each calibration image of the series taken in step i.) at least one key calibration figure characteristic for a tone mapping function of the mobile device; iii.) determining at least one probable tone mapping function of the mobile device by taking into account the key calibration figures from the calibration images of the series taken in step i.);
  iv.) prompting the user to take at least one analysis image of at least part of a test field of an optical test strip, the test field having the bodily fluid applied thereto; and
  v.) determining a concentration of an analyte in a bodily fluid from the analysis image of the test field by taking into account the probable tone mapping function of the mobile device.

Embodiment 53: The mobile device according to the preceding embodiment, wherein the mobile device, specifically the processor, is configured to perform the steps of a method according to any one of the preceding claims referring to a method of determining a concentration of an analyte in a bodily fluid by using a mobile device having a camera.

Embodiment 54: A kit for determining a concentration of an analyte in a bodily fluid, the kit comprising:
  at least one mobile device according to any one of the preceding claims referring to a mobile device; and
  at least one optical test strip having at least one test field.

Embodiment 55: The kit according to the preceding embodiment, wherein the optical test strip further comprises at least one region of interest.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
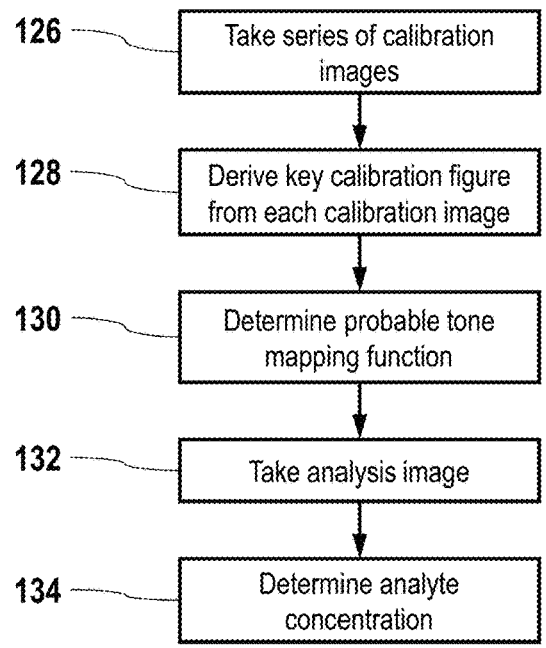
FIG. 1 shows a flow chart illustrating a method of determining a concentration of an analyte in a bodily fluid.
Figure 8:
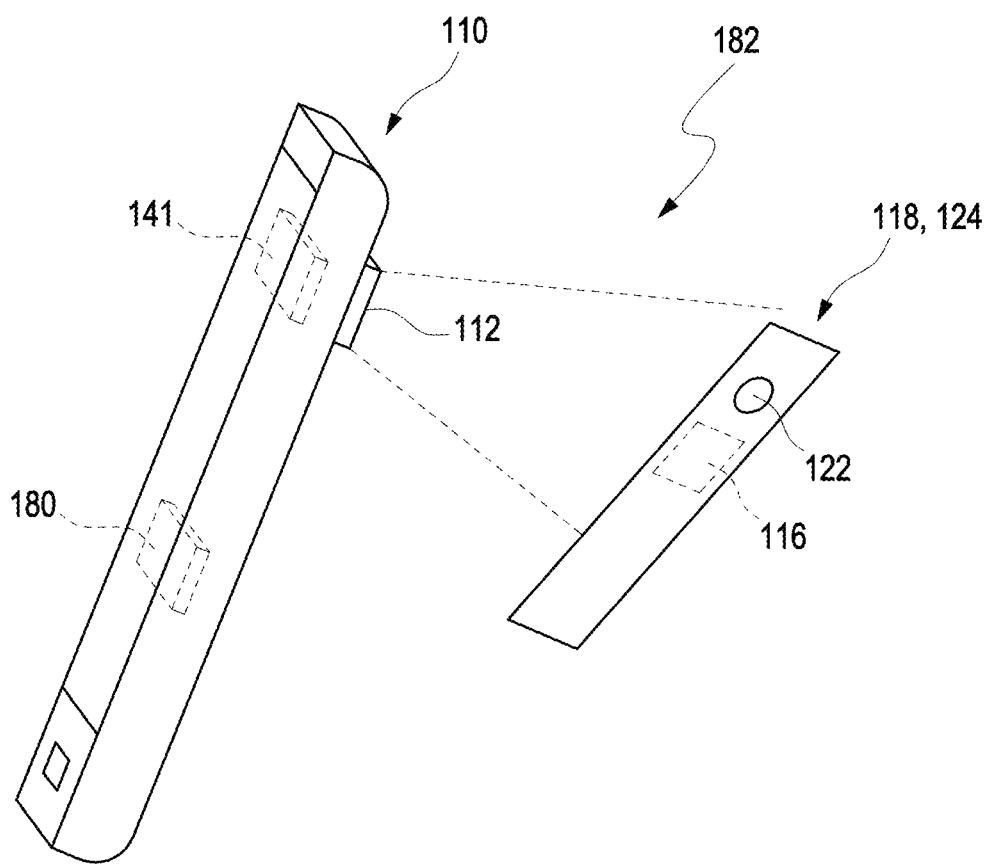
FIG. 8 shows a kit comprising a mobile device and an optical test strip.

In a first aspect of this disclosure a method of determining a concentration of an analyte in a bodily fluid by using a mobile device 110 having a camera 112 is disclosed. FIG. 1 shows a flow chart of the method, wherein components of the mobile device 110 are shown in FIG. 8. Further details of the method are shown in FIGS. 2 to 7B. In the following, reference is made to all of these Figures.

The method comprises the following steps, which may specifically be performed in the given order. Still, a different order may also be possible. It may further be possible to perform two or more of the method steps fully or partially simultaneously. It may further be possible to perform one or more method steps or even all of the method steps once or repeatedly. The method may comprise additional method steps which are not listed herein. The method steps are the following:

a) taking a series of calibration images 114, see, e.g., FIG. 4A, of at least one region of interest 116 of an object 118 by using the camera 112, see FIG. 8, wherein the calibration images 114 differ in their brightness;

b) deriving from each calibration image of the series taken in step a) at least one key calibration figure characteristic for a tone mapping function of the mobile device 110;

c) determining at least one probable tone mapping function 120, see, e.g., FIGS. 2, 4B, 5A, 5B, 6A, 7A and 7B, of the mobile device 110 by taking into account the key calibration figures from the calibration images 114 of the series taken in step a);

d) taking at least one analysis image of at least part of a test field 122 of an optical test strip 124, the test field 122 having the bodily fluid applied thereto, see, e.g., FIG. 8; and e) determining the concentration of the analyte in the bodily fluid from the analysis image of the test field 122 by taking into account the probable tone mapping function 120 of the mobile device 110.

In the flow chart shown in FIG. 1, step a) is represented by reference number 126, step b) is represented by reference number 128, step c) is represented by reference number 130, step d) is represented by reference number 132 and step e) is represented by reference number 134.

Figure 2:
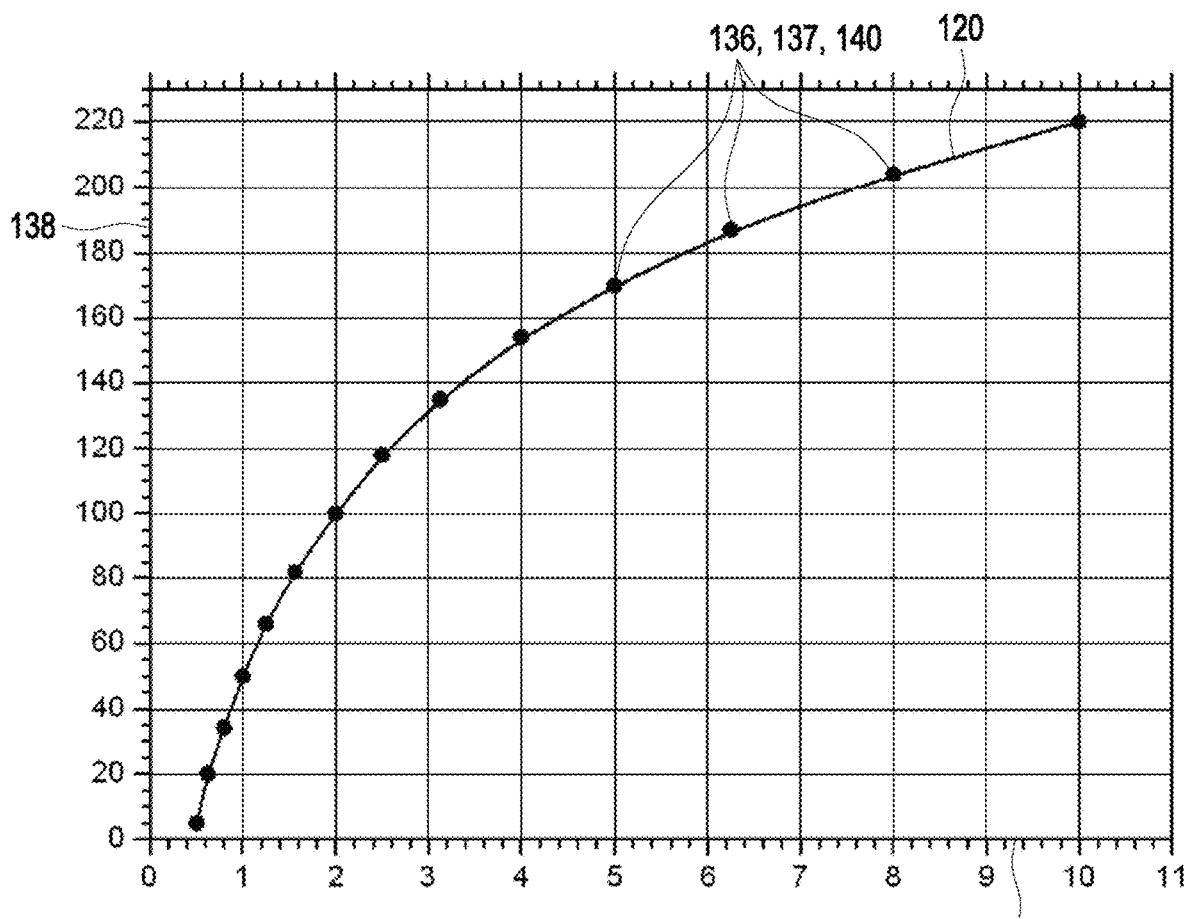
FIG. 2 shows a probable tone mapping function determined as described in step c) of the method.
Figure 3:
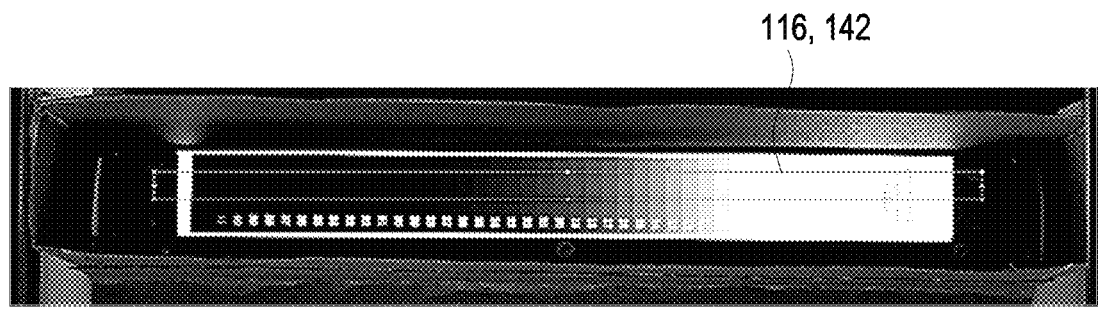
FIGS. 3A and 3B show a grey scale step wedge (3A) and a number of sampling points (3B) determined from a series of calibration images taken using the grey scale step wedge.
Figure 3:
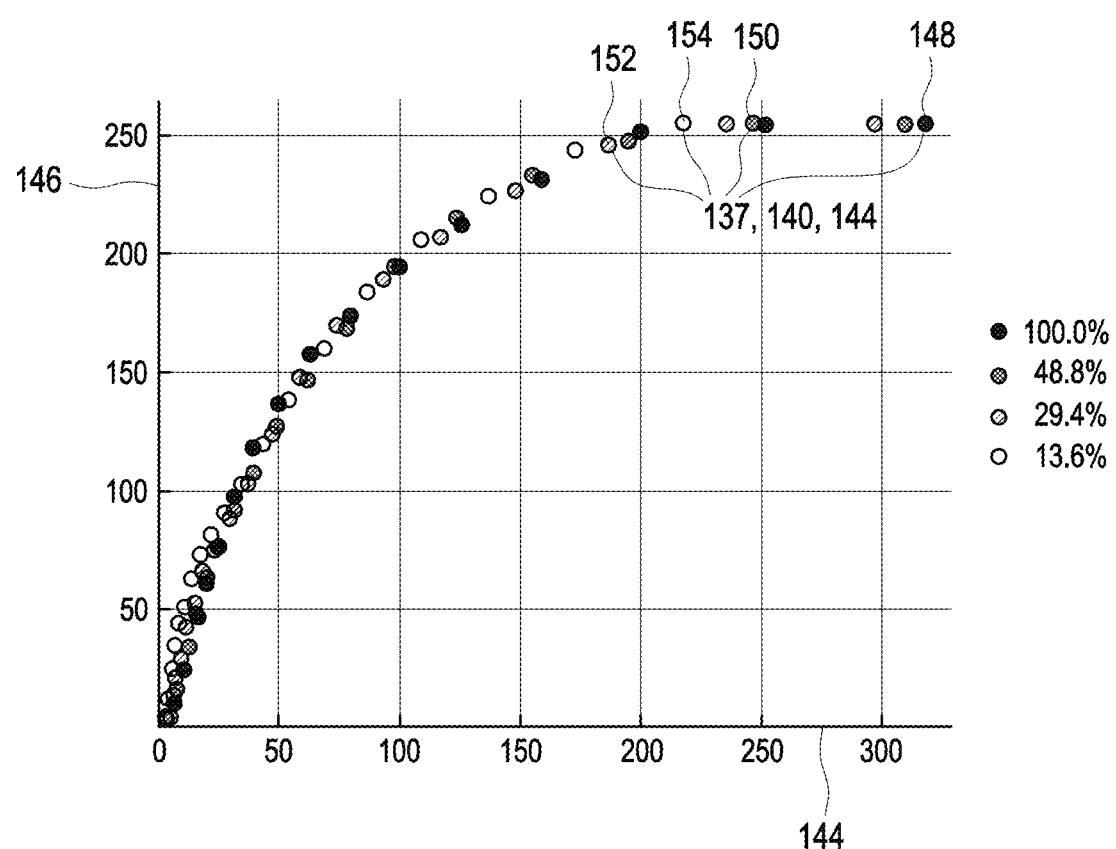
Figure 4:
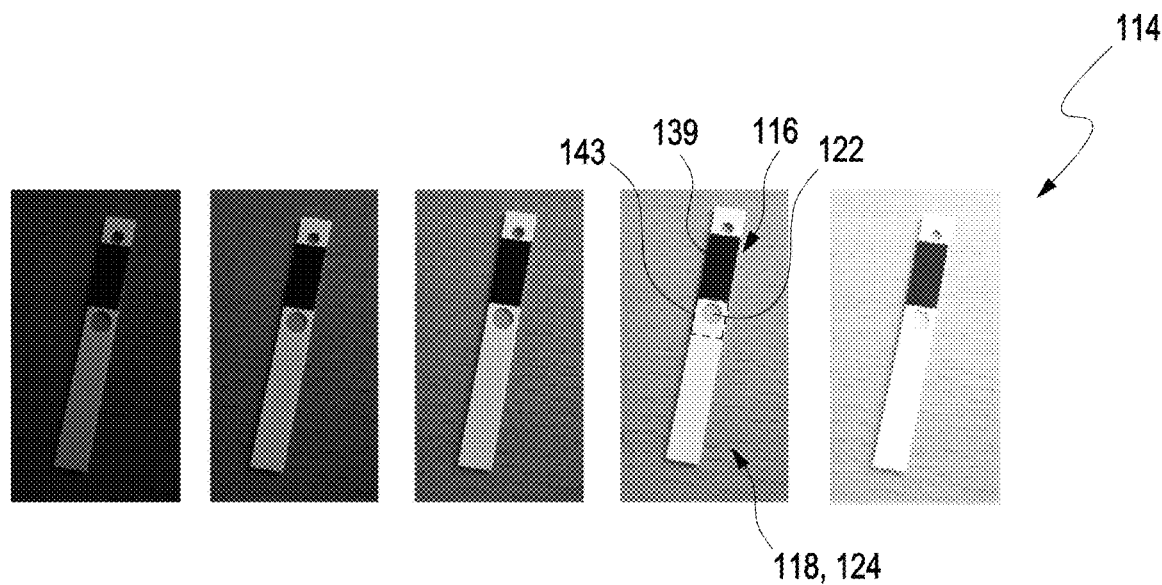
FIGS. 4A and 4B show a series of calibration images (4A) and a probable tone mapping function (4B) determined in part from the series of calibration images shown in FIG. 4A.
Figure 4:
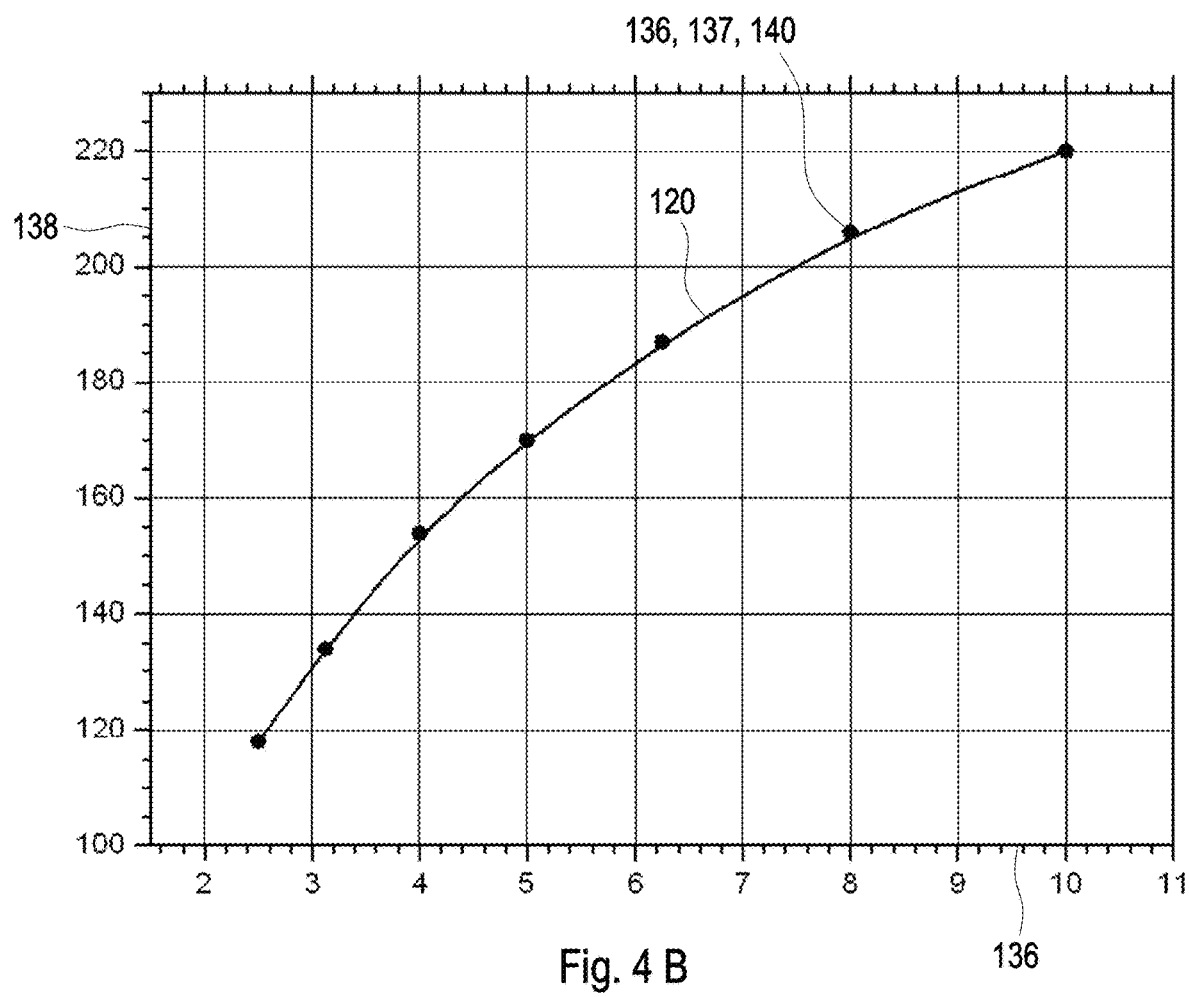
Figure 5:
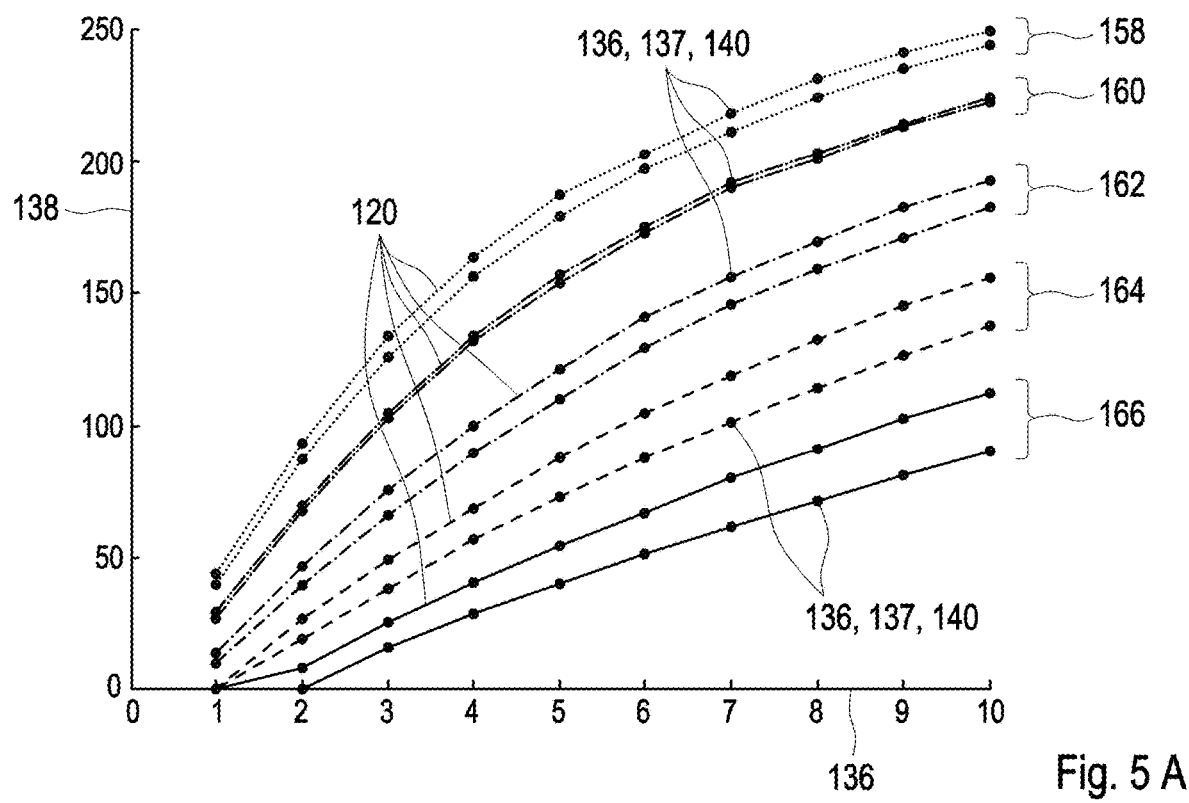
FIGS. 5A and 5B each show a number of different probable tone mapping functions, wherein in 5A the exposure time is varied while in 5B the ISO sensitivity of the camera is varied for the generation of the calibration images on which the probable tone mapping function is based.
Figure 5:
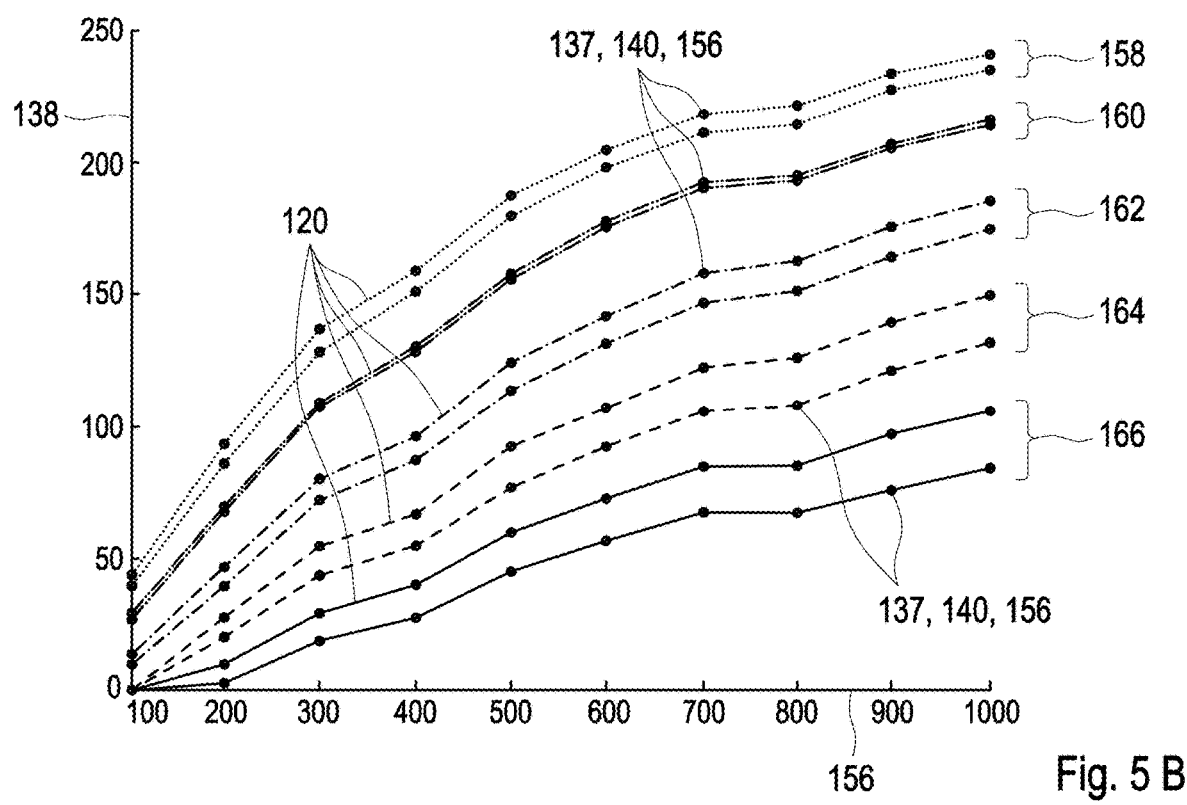
Figure 6:
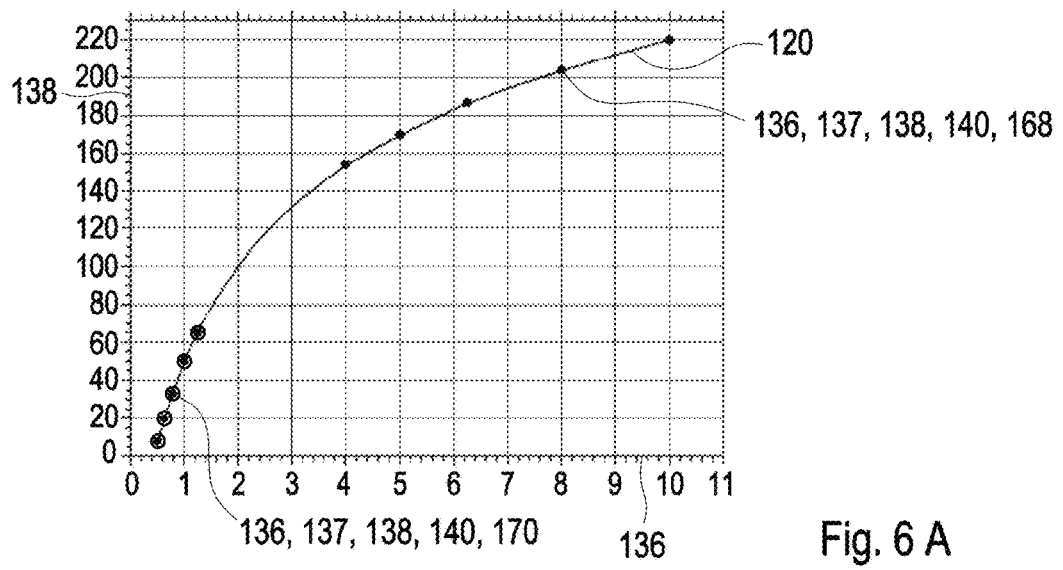
FIGS. 6A, 6B and 6C show a probable tone mapping function determined as described in step c) (6A), the probable tone mapping function of FIG. 6A after compensation of the sRGB gamma correction (6B), and a parabolic fit (6C) approximating the curve shown in FIG. 6B.
Figure 6:
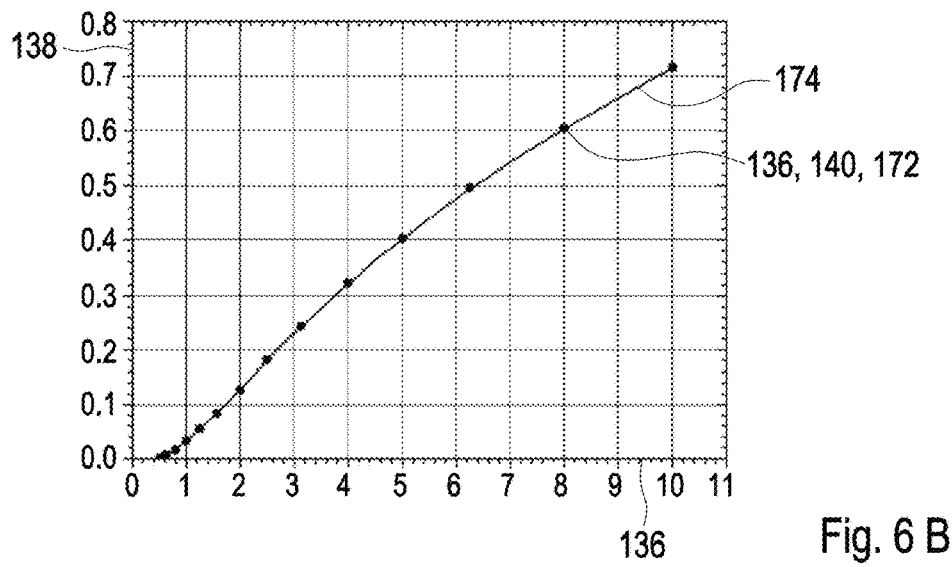
Figure 6:
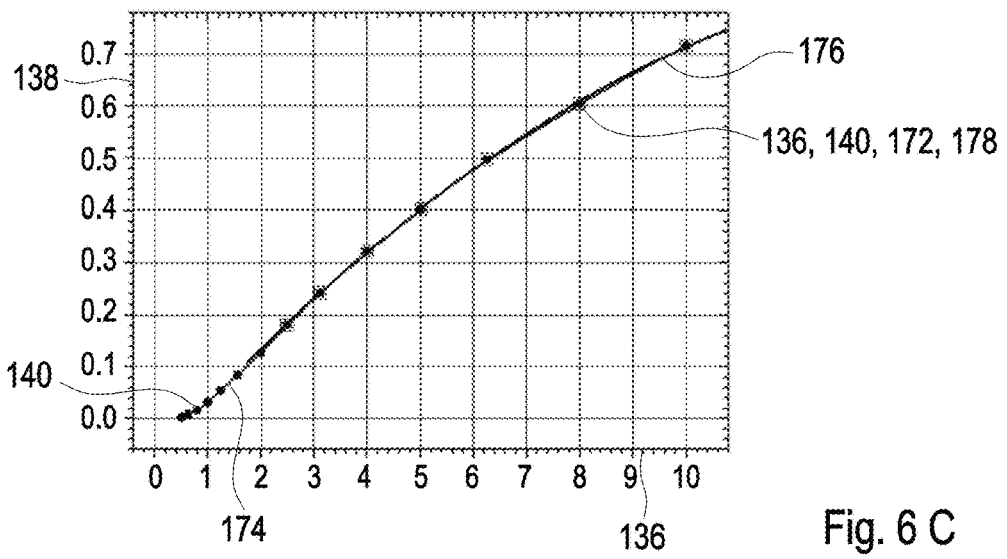
Figure 7:
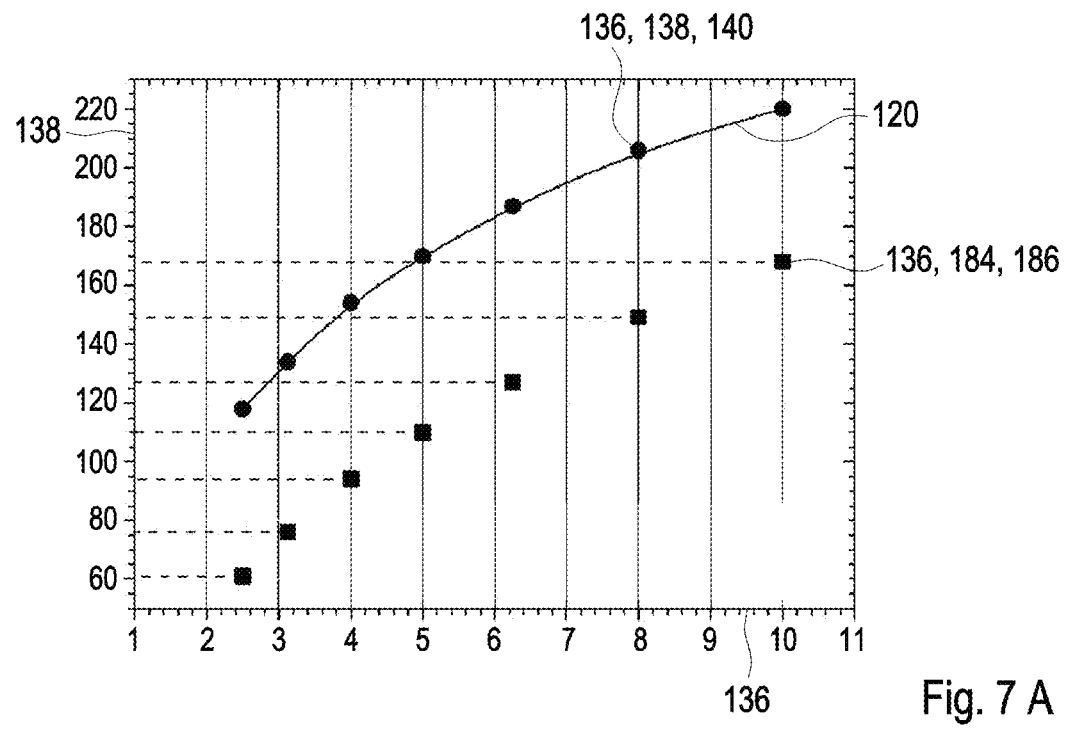
FIGS. 7A and 7B show a probable tone mapping function determined as described in step c) as well as pairs of values determined by an exposure time of the camera and a corresponding brightness value of a test field as part of a data set of an analysis image (7A) and the data of FIG. 7A depicted with the brightness values on a logarithmic scale (7B)
Figure 7:
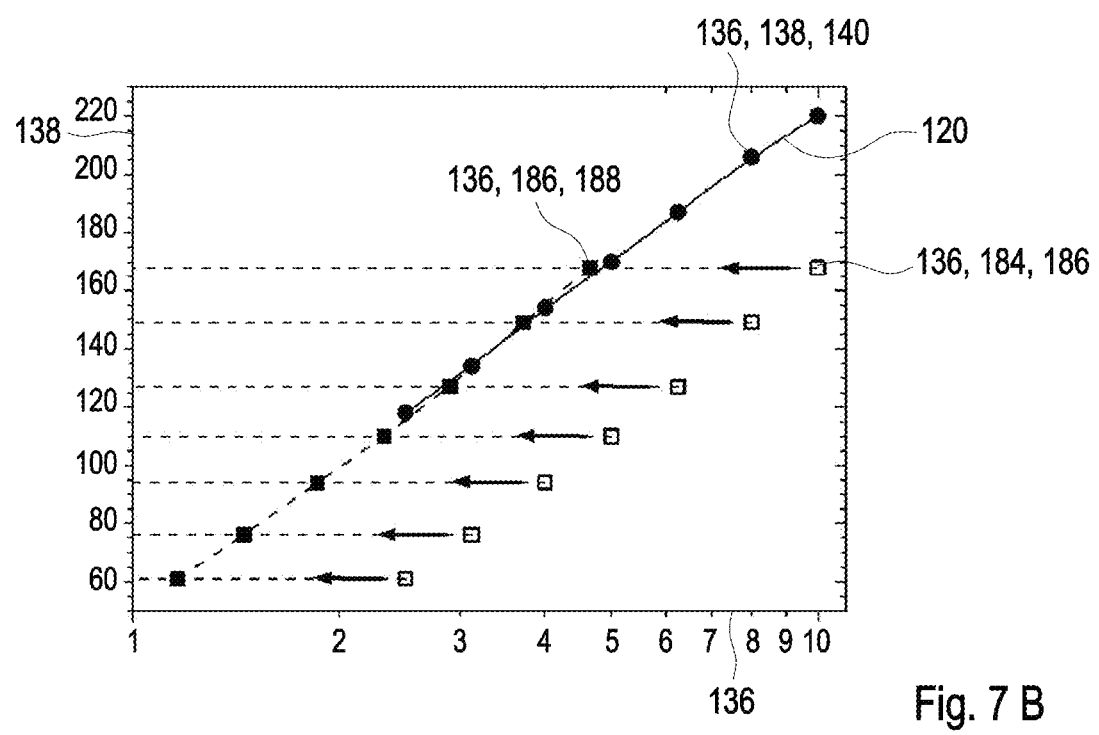

FIG. 2 shows a typical probable tone mapping function 120 as determined according to step c) of the method of determining a concentration of an analyte in a bodily fluid. The x-axis of the diagram of FIG. 2 shows an exposure time 136 in milliseconds. The y-axis of the diagram of FIG. 2 shows a brightness value 138 of a white field 143, the white field being the region of interest 116 in the case shown in FIG. 2. Other regions of interest are possible, e.g., a black field 139, a grey field and a grey scale step wedge 142. The calibration images 114 differ in their brightness. In step a), the brightness of the calibration images 114 may be actively varied, specifically in a stepwise fashion. In the case shown in FIG. 2, the brightness of the calibration images 114 is varied by varying the exposure time 136 of the camera 112 of the mobile device 110. The mobile device 110 may use the tone mapping function to assign to each brightness value 138 generated as raw data by an imaging device 141 of the camera 112 a brightness value 138 that may be part of an image file as processed data of the calibration image 114. The processed brightness value 138 may be derived from the calibration image and serve as the key calibration figure. The data set comprising the processed data of the calibration image 114 may be accessible, e.g., to the user.

Both the raw data and the tone mapping function of the mobile device 110 may not be known. To determine the probable tone mapping function 120 of the mobile device 110, the processed brightness value 138 may be derived from each data set comprising the processed data of the calibration image 114. The processed brightness value 138 of the calibration image 114 and a parameter value of the camera 112 used for the generation of the calibration image 114, which in the case of FIG. 2 is the exposure time 136, may together form a sampling point 140. FIG. 2 shows a total number of 14 sampling points 140. The probable tone mapping function 120 may be determined using the key calibration figures, in particular the processed brightness values 138, specifically the sampling points 140. In particular, the probable tone mapping function may be determined by fitting a function to the sampling points 140.

FIG. 3A shows a grey scale step wedge 142, which may serve as the region of interest 116. The x-axis of the diagram of FIG. 3B shows a grey scale value 144. The grey scale value 144 of the grey scale step wedge may change in a stepwise fashion. The y-axis of the diagram of FIG. 3B shows a value of the red channel 146, specifically an intensity of the red color channel, of the RGB color space. Other color channels may also be used. FIG. 3B further shows four sets of sampling points. For each set a different neutral density filter is used having filtering values of 100%, 48.8%, 29.4% and 23.6%. The sampling points 140 shown in FIG. 3B may comprise the grey scale value 144 of at least one of the fields of the grey scale step wedge 142 as an x-coordinate and the processed value of the red color channel 146 of the calibration image 114 as the y-coordinate. The sampling points acquired with the neutral density filter of 100% are referenced with reference number 148. The sampling points acquired with the neutral density filter of 48.8% are referenced with reference number 150. The sampling points acquired with the neutral density filter of 29.4% are referenced with reference number 152. The sampling points acquired with the neutral density filter of 13.6% are referenced with reference number 154. Each of the sets may be used for determining the probable tone mapping function 120.

FIG. 4A shows an exemplary series of calibration images 114, the object 118 in this case being the optical tests strip 124 comprising the test field 122 as well as the region of interest 116, which may, e.g., be the white field 143 or the black field 139. The exposure time 136 of the different calibration images 114 may differ. Thus, the exposure time 136 of the first and second calibration image 114 to the far left and left of the series shown in FIG. 4A may be 0.25 and 0.5 times the exposure time of the third calibration image in the middle of the series, while the exposure time of the fourth and fifth calibration image to the right and far right of the series may be 2 and 4 times the exposure time of the third calibration image 114 in the middle of the series. As described above, the term "image" may specifically refer to a set of spatially resolved optical data. Particularly in the case of FIG. 4A the graphical representation of the data set may also be referred to as the image.

FIG. 4B shows a further exemplary probable tone mapping function 120 determined using a series of calibration images 114, which differ in their exposure time 136. The x-axis of the diagram of FIG. 4B shows the exposure time 136 in ms. The y-axis of the diagram of FIG. 4B shows the brightness value 138 of the white field. The probable tone mapping function 120 is determined using seven sampling points 140. Each sampling point 140 may comprise the exposure time 136 at which the calibration image 114 is taken as the x-coordinate and the processed value of the brightness value 138 of the region of interest 116, specifically the white field 143, of the calibration image 114 generated with the exposure time 136.

FIGS. 5A and 5B show probable tone mapping functions 120 as determined using the method according to this disclosure. The brightness of the calibration images 114 of the series of calibration images 114 differs according to step a). In the case of FIG. 5A, the brightness of the calibration images 114 is actively varied by varying the exposure time 136 while the ISO sensitivity of the camera is kept constant at a value of 100. In the case of FIG. 5B the brightness of the calibration images 114 is actively varied by varying the ISO sensitivity of the camera 112 while the exposure time 136 is kept constant at 1 ms. In both cases, the mobile device used is a Samsung J7 and the red color channel is used to derive the key calibration FIG. 137 in the form of the brightness value 138 of the red color channel. For both 5A and 5B a grey field serves as region of interest 116. Five sets of data with each set comprising two probable tone mapping functions 120 are shown in both FIGS. 5A and 5B. The sets correspond to different grey levels of the grey field, which have different brightness values 138. The grey levels with the relative brightness values of 20%, 30%, 40%, 50% and 60% are referenced with reference number 158, 160, 162, 164 and 166 respectively. In particular, the relative brightness values given in %, may specifically indicate a proportion or percentage of black mixed with white. Thus, a gray level with the relative brightness value of 20% may for example indicate a gray level with 20% black and 80% white. The sampling points 140 displayed in FIG. 5A may comprise the exposure time 136 at which the calibration image 114 is taken as x-coordinate and the processed brightness value 138 of the grey field of the calibration image 114 as the y-coordinate. The sampling points 140 displayed in FIG. 5B may comprise the ISO sensitivity of the camera, particularly the imaging device 141, with which the calibration image 114 is taken as x-coordinate and the processed brightness value 138 of the grey field of the calibration image 114 as the y-coordinate. FIGS. 5A and 5B further show the probable tone mapping functions 120 as determined according to step c) of the method. The active variation of the exposure time 136 delivers the more consistent results than the active variation of the ISO sensitivity, particularly in the form of smoother tone mapping curves 120, as can be seen by comparing FIGS. 5A and 5B.

Step a) of the method comprises taking the series of calibration images 114 of the at least one region of interest 116 of the object 118. The object 118 may also comprise a plurality of the regions of interest 116, e.g., two regions of interest 116 such as one white field 143 and one black field 139. FIG. 6A shows a probable tone mapping function 120 determined according to step c) of the method. The key calibration figures taken into account in step c) may be the brightness values 138 derived from the calibration images 114 taken in step a), as is the case for FIG. 6A. The brightness values 138 may specifically be the processed brightness values 138 generated by the mobile device by applying the tone mapping function to the brightness values detected by the imaging device 141 of the camera 112. The processed brightness 138 values may form part of the sampling points 140, as can be seen in FIG. 6A. In particular, the processed brightness values 138, which may be part of or derived from the data set of the calibration image 114, may be the y-coordinate of the sampling point 140, as shown in FIG. 6A. Further, the exposure time 136 of the calibration images 114 may be varied to vary the brightness of the calibration images 114. Specifically, the sampling point 140 may comprise the exposure time 136 of the calibration image 114 as the x-coordinate, as illustrated in FIG. 6A. The diagram displayed in FIG. 6A plots the processed brightness value 138 of the calibration image 114 on the y-axis versus the exposure time 136 on the x-axis. The diagram of FIG. 6A shows five sampling points 140 whose key calibration FIG. 137, in particular the brightness value 138 used as y-coordinate, is derived from a calibration image 114 generated by the stepwise underexposure of the white field 143 of the object 118. These sampling points 140 are further marked by reference number 168. The diagram of FIG. 6A further shows five sampling points 140 whose key calibration FIG. 137, in particular the brightness value 138 used as y-coordinate, is derived from a calibration image 114 generated by the stepwise overexposure of the black field 139 of the object 118. These sampling points 140 are marked by reference number 170.

FIG. 6B shows the probable tone mapping function 120 of FIG. 6A after partial linearization achieved by application of the inverted sRGB gamma correction. In the diagram of FIG. 6B the brightness values 138 are plotted on the y-axis and the exposure time 136 is plotted on the x-axis. As becomes apparent from a resulting function 174 displayed in FIG. 6B, the resulting function 174 shows some residual non-linearity such that the probable tone mapping function 120 determined according to step c) and displayed in FIG. 6A may not be identical to the sRGB gamma correction. Thus, the tone mapping function actually used by the mobile device 110 may not be identical to the sRGB correction.

In FIG. 6B, the brightness values 138 after application of the sRGB gamma correction are further marked with reference number 172. The sampling points 140 of the resulting function 174 may comprise the brightness values 138 after application of the inverted gamma correction 172 as y-coordinates and the exposure time 136 of the corresponding calibration image 114 as x-coordinates. The probable tone mapping function 120 may be the tone mapping function that is likely used by the mobile device 110, e.g., by applying the tone mapping function to the data set generated by the imaging device 141 of the camera 112. The probable tone mapping function 120 may alternatively approximate the tone mapping function that is actually used by mobile device 110. As part of the determination of the probable tone mapping function 120, the resulting function 174 or at least a section thereof may be approximated, e.g., by a parabolic fit 176, as illustrated in FIG. 6C. A relevant section of the resulting function 174, which may comprise the brightness values 138 suitable for determining the analyte concentration from the analysis image of the test field 122. The sampling points 140 comprised by the relevant section in FIG. 6C are marked with boxes and the reference number 178. Thus, it may be possible to describe a deviation of the probable tone mapping function 120 from the sRGB gamma correction by a single parameter, e.g., a quadratic term. Additionally, further terms may be used such as terms of higher order, e.g., a term of third order.

Step e) of the method comprises determining the concentration of the analyte in the bodily fluid from the analysis image of the test field 122 by taking into account the probable tone mapping function 120 of the mobile device 110. In step e) the analyte concentration may specifically be determined from a brightness ratio between the test field 122 having the bodily fluid applied and the region of interest 116 of the object 118. The brightness ratio between the test field 122 with the bodily fluid applied and the region of interest 116 may be unknown and may have to be determined. In particular, it may not be possible to determine said brightness ratio by dividing the respective brightness values 138 as available from the processed data set of the analysis image and the processed data set of the calibration image 114 due to the non-linearity of the tone mapping curve applied by the mobile device 110.

FIGS. 7A and 7B illustrate an optional way of determining, in particular approximating, the brightness ratio between the test field 122 having the bodily fluid applied and the region of interest 116. FIG. 7A shows a diagram with the exposure time 136 being plotted on the x-axis and the brightness values plotted on the y-axis. The diagram displays the probable tone mapping function 120 as determined using the sampling points 140, which are likewise indicated. As the y-coordinate, the sampling points 140 may comprise the key calibration figure, in this case specifically the brightness value 138 of the white field 143 serving in this case as the region of interest 116, the brightness value 138 being derived from the processed data set of the calibration image 114. As the x-coordinate, the sampling points 140 may comprise the exposure time 136 used for taking the calibration image 114. Further indicated in FIG. 7A are analysis points 184 determined by a y-coordinate, which may be the key analysis FIG. 186, specifically the brightness value 138 of the test field 122 with the bodily fluid applied as may be derived from the processed data set of the analysis image, and an x-coordinate, specifically the exposure time 136 used for taking the analysis image. Specifically, the data shown in FIG. 7A may be acquired simultaneously. Specifically, each analysis image may coincide with one of the calibration images 114.

FIG. 7B shows the data displayed in FIG. 7A, specifically the probable tone mapping function 120, the sampling points 140 and the analysis points 184, with the x-axis in a logarithmic scale. FIG. 7B further indicates with arrows that the analysis points 184 may be shifted onto the probable tone mapping function 120 or its extrapolation by adapting their x-coordinate. Shifting may specifically be achieved for all analysis points 184 by multiplying the x-coordinates of the analysis points 184 with a common deviation factor. The deviation factor may be specific for or may reflect the brightness ratio between the test field 122 having the bodily fluid applied and the region of interest 116 of the object 118. In the diagram of FIG. 7B the deviation factor may be 0.465. The shifted analysis points are marked with reference number 188.

The brightness ratio of the test field 122 with the bodily fluid applied and the region of interest 116 may be set in relation to a reference brightness ratio. The reference brightness ratio may for example be the brightness ratio between the test field 122 without the bodily fluid applied and the region of interest 116. Alternatively, the reference brightness ratio may be the brightness ratio between a reference field on the optical test strip 124 and the region of interest 116. From the ratio between the two brightness ratios, e.g., the brightness ratio between the test field 122 having the bodily fluid applied and the region of interest 116 of the object 118 and the reference brightness ratio, the analyte concentration may be determined such as by using at least one of: a code curve; a look-up table; a neuronal network (not shown in the Figures).

As outlined above, in FIG. 8, an embodiment of a mobile device 110 is shown in a perspective view, the mobile device 110 having a camera 112 and at least one processor 180. The processor 180 is configured, e.g., by programming, to perform the following steps:

i.) prompting a user to take a series of calibration images 114 of at least one region of interest 116 of an object 118 by using the camera 112, wherein the calibration images 114 differ in their brightness;

ii.) deriving from each calibration image 114 of the series taken in step i.) at least one key calibration FIG. 137 characteristic for a tone mapping function of the mobile device 110;

iii.) determining at least one probable tone mapping function 120 of the mobile device 110 by taking into account the key calibration FIG. 137 from the calibration images 114 of the series taken in step i.);

iv.) prompting the user to take at least one analysis image of at least part of a test field 122 of an optical test strip 124, the test field 122 having the bodily fluid applied thereto; and determining a concentration of an analyte in a bodily fluid from the analysis image of the test field 122 by taking into account the probable tone mapping function 120 of the mobile device 110.

FIG. 8 further shows an embodiment of a kit 182 for determining a concentration of an analyte in a bodily fluid is disclosed, the kit 182 comprising:

at least one mobile device 110 having a camera 110 and at least one processor 180 as described above or as further described below; and at least one optical test strip 124 having at least one test field 122.

The optical test strip 124 may in particular comprise at least one region of interest 116.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 mobile device
112 camera 114 calibration image
116 region of interest
118 object
120 probable tone mapping function
122 test field
124 optical test strip
126 step a)
128 step b)
130 step c)
132 step d)
134 step e)
136 exposure time
137 key calibration FIG.
138 brightness value
139 black field
140 sampling point
141 imaging device
142 grey scale step wedge
143 white field
144 grey scale value
146 value of red color channel
148 neutral density filter of 100%
150 neutral density filter of 48.8%
152 neutral density filter of 29.4%
154 neutral density filter of 13.6%
156 ISO sensitivity
158 grey level with relative brightness value of 20%
160 grey level with relative brightness value of 30%
162 grey level with relative brightness value of 40%
164 grey level with relative brightness value of 50%
166 grey level with relative brightness value of 60%
168 underexposure of the white field
170 overexposure of the black field
172 brightness values after application of inverted gamma correction
174 resulting function
176 parabolic kit
178 sampling points of the relevant section of the resulting function
180 processor
182 kit
184 analysis point
186 key analysis figure
188 shifted analysis point

What is claimed is:

1. A method of determining concentration of an analyte in a body fluid using a mobile device having a camera, the method comprising:
   a) using the camera to take a series of calibration images of a region of interest of an object, wherein the calibration images differ in their brightness, and wherein the mobile device automatically applies to the calibration images a tone mapping function that renders the images taken by the camera less suitable for analytical measurements;
   b) deriving from each calibration image a key calibration figure characteristic for the tone mapping function;
   c) using the key calibration figures derived in step b) to approximate the tone mapping function;
   d) taking an analysis image of at least part of a test field of an optical test strip, the test field having the body fluid applied thereto; and
   e) determining the concentration of the analyte in the body fluid from the analysis image of the test field while taking into account the approximated tone mapping function, whereby the accuracy of the determined analyte concentration is improved by correcting for the effect of the tone mapping function.

2. The method according to claim 1, wherein steps d) and e) are performed repeatedly.

3. The method according to claim 2, wherein steps a)-c) are performed only once initially for a plurality of repetitions of steps d) and e), or each time before performing steps d) and e), or at a predetermined frequency.

4. The method according to claim 1, wherein the object comprises the optical test strip, wherein the analysis image coincides with at least one of the calibration images, whereby that the analysis image is taken as part of the series of calibration images.

5. The method according to claim 1, wherein the region of interest is selected from the group consisting of a white field, a black field, a grey field and a grey scale step wedge.

6. The method according to claim 1, wherein each calibration image comprises at least two regions of interest, wherein a physical brightness ratio between the two regions of interest is known.

7. The method according to claim 1, wherein for each calibration image the key calibration figure is derived from at least one brightness value of the region of interest of the calibration image.

8. The method according to claim 1, wherein the brightness of the calibration images is varied in step a) by varying a parameter value of at least one of the following parameters: exposure time, light sensitivity of an image sensor of the camera, and light intensity of an illuminant.

9. The method according to claim 8, wherein step c) comprises determining at least one sampling point for each calibration image, wherein the sampling point comprises the key calibration figure and the parameter value.

10. The method according to claim 9, wherein step c) comprises determining the approximated tone mapping function by at least one of the following: (i) determining a fit curve for the sampling points of the series of calibration images, and (ii) choosing a function from a predetermined set of functions, wherein the chosen function fits the sampling points of the series of calibration images.

11. The method according to claim 1, wherein step e) comprises deriving a key analysis figure from a brightness value of at least one part of the analysis image showing the at least one part of the test field.

12. The method according to claim 11, wherein from each key analysis figure at least one probable analyte measurement figure is derived by applying an inverted probable tone mapping function to the key analysis figure.

13. The method according to claim 1, wherein in step e) the analyte concentration is determined from a brightness ratio between the test field having the body fluid applied and the region of interest of the object.

14. A non-transitory computer readable medium having stored thereon computer executable instructions for performing the method according to claim 1.

15. The method according to claim 1, wherein the series of calibration images are taken with the built-in camera of the mobile device and are unaugmented by external devices.

16. A mobile device having a camera and a processor, the processor configured to:
   prompt a user to take a series of calibration images of a region of interest of an object by using the camera, wherein the calibration images differ in their brightness, and wherein the mobile device automatically applies to the calibration images a tone mapping function that renders the images taken by the camera less suitable for analytical measurements;

derive from each calibration image a key calibration figure characteristic for the tone mapping function of the mobile device;

use the derived key calibration figures to approximate the tone mapping function;

prompt the user to take an analysis image of at least part of a test field of an optical test strip, the test field having a body fluid applied thereto; and determining the concentration of the analyte in the body fluid from the analysis image of the test field by while taking into account the approximated tone mapping function, whereby the accuracy of the determined analyte concentration is improved by correcting for the effect of the tone mapping function.

17. A kit for determining concentration of an analyte in a body fluid, the kit comprising:

a mobile device according to claim 16; and an optical test strip having at least one test field.

18. The method according to claim 16, wherein the series of calibration images are taken with the built-in camera of the mobile device and are unaugmented by external devices.

\* \* \* \* \*